(12) United States Patent
Yao

(10) Patent No.: US 11,306,062 B2
(45) Date of Patent: Apr. 19, 2022

(54) FORMS OF FEDRATINIB DIHYDROCHLORIDE

(71) Applicant: Johnson Matthey Public Limited Company, London (GB)

(72) Inventor: Na Yao, Devens, MA (US)

(73) Assignee: Johnson Matthey Public Limited, London (GB)

( * ) Notice: Subject to any disclaimer, the term of this patent is extended or adjusted under 35 U.S.C. 154(b) by 0 days.

(21) Appl. No.: 17/084,154

(22) Filed: Oct. 29, 2020

(65) Prior Publication Data

US 2021/0122718 A1    Apr. 29, 2021

Related U.S. Application Data

(60) Provisional application No. 62/927,455, filed on Oct. 29, 2019.

(51) Int. Cl.
*C07D 239/48* (2006.01)
*C07D 239/69* (2006.01)

(52) U.S. Cl.
CPC ......... *C07D 239/69* (2013.01); *C07D 239/48* (2013.01); *C07B 2200/13* (2013.01)

(58) Field of Classification Search
CPC .......................... C07D 403/12; A61K 31/506
USPC .......................................... 544/332; 514/275
See application file for complete search history.

(56) References Cited

U.S. PATENT DOCUMENTS 7,528,143 B2    5/2009   Noronha et al.
7,825,246 B2    11/2010  Noronha et al.
10,391,094 B2   8/2019   Jayan et al.

*Primary Examiner* — Jeffrey H Murray

(57) ABSTRACT

The present disclosure relates to novel forms of fedratinib dihydrochloride (diHCl) and processes for the preparation of the various forms. The present disclosure also relates to pharmaceutical compositions comprising the novel forms of fedratinib dihydrochloride and methods for treating disease using the forms.

5 Claims, 32 Drawing Sheets

FORMS OF FEDRATINIB DIHYDROCHLORIDE

CROSS REFERENCE TO RELATED APPLICATIONS

This application claims priority to U.S. Provisional Patent Application No. 62/927,455, filed on Oct. 29, 2019, the contents of which are hereby incorporated in its entirety.

FIELD OF THE DISCLOSURE

The present disclosure relates to novel forms of fedratinib dihydrochloride (diHCl) and processes for the preparation of the various forms. The present disclosure also relates to pharmaceutical compositions comprising the novel forms of fedratinib dihydrochloride and methods for treating disease using the forms.

BACKGROUND OF THE DISCLOSURE

Fedratinib, having the chemical designation N-tert-butyl-3-[[5-methyl-2-[4-(2-pyrrolidin-1-ylethoxy)anilino]pyrimidin-4-yl]amino]benzenesulfonamide, is an oral kinase inhibitor with activity against wild type and mutationally activated Janus Associated Kinase 2 (JAK2) and FMS-like tyrosine kinase 3 (FLT3). Fedratinib has the following structure:

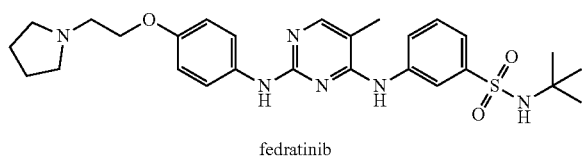 [SMILES: Cc1cnc(Nc2ccc(OCCN3CCCC3)cc2)nc1Nc1cccc(S(=O)(=O)NC(C)(C)C)c1]

fedratinib

Fedratinib is a highly selective JAK2 inhibitor intended for the treatment of patients with myelofibrosis, a serious bone marrow disorder that disrupts the body's normal production of blood cells. Fedratinib, marketed under the brand INREBIC®, is indicated for the treatment of adult patients with intermediate-2 or high-risk primary or secondary (post-polycythemia vera or post-essential thrombocythemia) myelofibrosis Off).

U.S. Pat. Nos. 7,528,143 and 7,825,246 disclose fedratinib and/or a process used to prepare it. Neither of these references disclose particular solid-state forms of fedratinib diHCl, including fedratinib diHCl co-crystals.

SUMMARY OF THE DISCLOSURE

The present invention is directed to crystalline forms of fedratinib diHCl, designated herein as Forms A-F, amorphous fedratinib diHCl, a fedratinib diHCl co-crystal with succinic acid, a fedratinib diHCl co-crystal with fumaric acid, and a fedratinib diHCl co-crystal with sucrose. The present invention is further directed to processes for the preparation of these forms. The present invention also is directed to pharmaceutical compositions comprising these forms, and to a method for treating disease using these forms.

DETAILED DESCRIPTION OF THE DISCLOSURE

Figure 1:
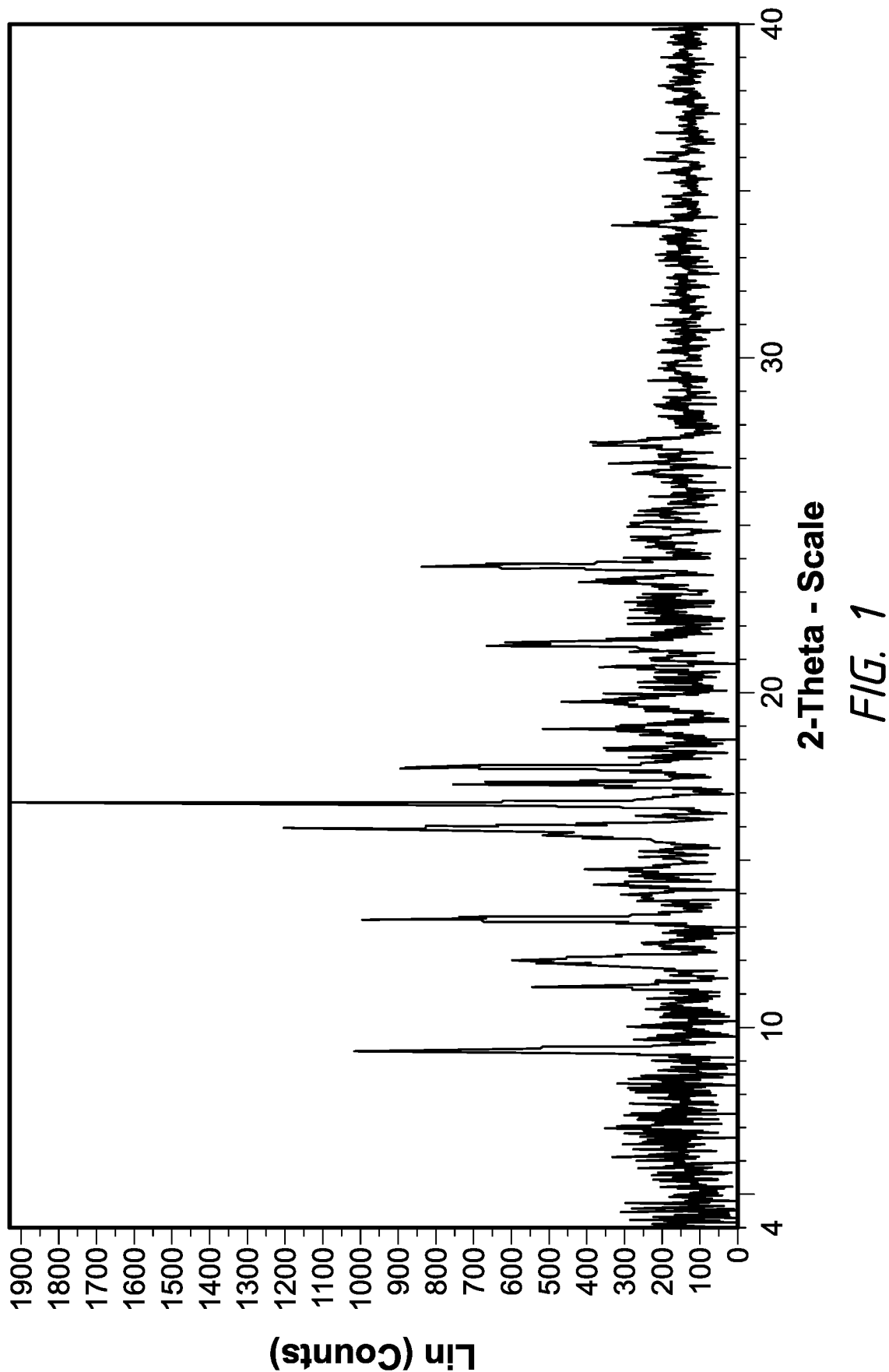
FIG. 1 is a representative XRPD pattern of Form A of fedratinib diHCl.

The present disclosure is directed to novel crystalline forms of fedratinib diHCl, designated herein as Forms A-F, amorphous fedratinib diHCl, a fedratinib diHCl co-crystal with succinic acid, a fedratinib diHCl co-crystal with fumaric acid, and a fedratinib diHCl co-crystal with sucrose; pharmaceutical compositions comprising these forms of fedratinib diHCl, processes for the preparation of these forms of fedratinib diHCl, and the use of these forms of fedratinib diHCl for treating a patient with myelofibrosis.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form.

As used herein and unless otherwise specified, the term "pharmaceutical composition" is intended to encompass a pharmaceutically effective amount of one or more of Forms A-F of fedratinib diHCl, amorphous fedratinib diHCl, a fedratinib diHCl co-crystal with succinic acid, a fedratinib diHCl co-crystal with fumaric acid, and a fedratinib diHCl co-crystal with sucrose and a pharmaceutically acceptable excipient. As used herein, the term "pharmaceutical compositions" includes pharmaceutical compositions such as tablets, pills, powders, liquids, suspensions, emulsions, granules, capsules, suppositories, or injection preparations.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23rd ed., 1843-1844 (1995).

As used herein and unless otherwise specified, the term "excipient" refers to a pharmaceutically acceptable organic or inorganic carrier substance. Excipients may be natural or synthetic substances formulated alongside the active ingredient of a medication, included for the purpose of bulking-up formulations that contain potent active ingredients (thus often referred to as "bulking agents," "fillers," or "diluents"), or to confer a therapeutic enhancement on the active ingredient in the final dosage form, such as facilitating drug absorption or solubility. Excipients can also be useful in the manufacturing process, to aid in the handling of the active substance, such as by facilitating powder flowability or non-stick properties, in addition to aiding in vitro stability such as prevention of denaturation over the expected shelf life.

As used herein and unless otherwise specified, the term "patient" refers to an animal, preferably a mammal, most preferably a human, who has been the object of treatment, observation or experiment. Preferably, the patient has experienced and/or exhibited at least one symptom of the disease or disorder to be treated and/or prevented. Further, a patient may not have exhibited any symptoms of the disorder, disease or condition to be treated and/or prevented, but has been deemed by a physician, clinician or other medical professional to be at risk for developing said disorder, disease or condition.

As used herein and unless otherwise specified, the terms "polymorph," "polymorphic form" or related term herein, refer to a crystal form of an API (active pharmaceutical ingredient) free base or salt thereof that can exist in two or more forms, as a result of different arrangements or conformations of the molecule, ions of the salt, or addition and arrangement of solvents or coformers within the crystalline lattice.

As used herein and unless otherwise specified, "co-crystal" and "co-crystal systems" refer to solid materials composed of two or more different components that are solid at room temperature and in particular stoichiometric ratios which interact through non-covalent interactions which can be designed utilizing supramolecular synthon approach. The co-crystal, in which at least one of the components is fedratinib diHCl and the coformer is a second pharmaceutically acceptable compound, is called a pharmaceutical fedratinib diHCl co-crystal with the coformer.

As used herein and unless otherwise specified, the terms "substantially" or "substantially free/pure" with respect to a polymorph or polymorphic form means that the form contains about less than 30 percent, about less than 20 percent, about less than 15 percent, about less than 10 percent, about less than 5 percent, or about less than 1 percent by weight of impurities. Impurities may, for example, include other polymorphic forms, water and solvents other than that in a solvated crystalline polymorphic form.

As used herein and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more therapeutic agents to a patient with such a disease or disorder. In some embodiments, the terms refer to the administration of a compound provided herein, with or without other additional active agents, after the onset of symptoms of the particular disease. Fedratinib is intended for the treatment of patients with myelofibrosis.

As used herein and unless otherwise specified, the term "room temperature" refers to about 20° C.±5° C.

It is therefore an object of the present disclosure to provide Forms A-F of fedratinib diHCl, amorphous fedratinib diHCl, a fedratinib diHCl co-crystal with succinic acid, a fedratinib diHCl co-crystal with fumaric acid, and a fedratinib diHCl co-crystal with sucrose that are substantially pure, stable and scalable. It is also an object of the present disclosure to provide Forms A-F of fedratinib diHCl, amorphous fedratinib diHCl, a fedratinib diHCl co-crystal with succinic acid, a fedratinib diHCl co-crystal with fumaric acid, and a fedratinib diHCl co-crystal with sucrose that are capable of being isolated and handled. It is further an object of the present disclosure to provide a process for the preparation of Forms A-F of fedratinib diHCl, amorphous fedratinib diHCl, a fedratinib diHCl co-crystal with succinic acid, a fedratinib diHCl co-crystal with fumaric acid, and a fedratinib diHCl co-crystal with sucrose. It is yet another object of the present disclosure to provide a method of use of Forms A-F of fedratinib diHCl, amorphous fedratinib diHCl, a fedratinib diHCl co-crystal with succinic acid, a fedratinib diHCl co-crystal with fumaric acid, and a fedratinib diHCl co-crystal with sucrose to prepare a pharmaceutical dosage form of fedratinib diHCl.

Techniques for characterizing crystal and amorphous forms include but are not limited to differential scanning calorimetry (DSC), thermal gravimetric analysis (TGA), dynamic vapor sorption (DVS), X-ray powder diffractometry (XRPD), single crystal X-ray diffraction (SCXRD), proton nuclear magnetic resonance ($^1$H-NMR), Fourier transform infrared spectroscopy (FTIR Spectroscopy), and Optical Microscopy.

DSC data are collected using a TA Instruments Q2000 DSC. Approximately, samples (2-5 mg) were placed in sealed hermetic aluminum sample pans and scanned from about 25 to 300° C. at a rate of about 10° C./min under a nitrogen purge of 50 mL/min. The modulated DSC (mDSC) is carried out with modulation ±0.5° C. every 60 s and measured from 5° C. to 120° C. at a heating rate of 1.5° C./min under a nitrogen purge of 50 mL/min.

TGA data are collected using a TA Instruments TGA Q500. Approximately, samples (2-5 mg) were placed in an open, pre-tared aluminum sample pan and scanned from about 25 to 350° C. at a rate of about 10° C./min using a nitrogen purge at about 60 mL/min.

XRPD patterns are obtained using a Bruker D8 Advance equipped with a Cu Kα radiation source (λ=1.54 Å), a 9-position sample holder and a LYNXEYE super speed detector. Samples are placed on zero-background, silicon plate holders for analysis. One skilled in the art would recognize that the ° 2θ values and the relative intensity values are generated by performing a peak search on the measured data and the d-spacing values are calculated by the instrument from the ° 2θ values using Bragg's equation. One skilled in the art would further recognize that the relative intensity for the measured peaks may vary as a result of sample preparation, orientation and instrument used, for example.

$^1$H-NMR data are collected using a Bruker Ascend 600 MHz NMR equipped with TopSpin software. Samples are prepared by dissolving the compound in deuterated dimethylsulfoxide with 0.05% (v/v) tetramethylsilane (TMS). Spectra are collected at 298 K.

KF data are measured using a Mettler Toledo DL32 Karl Fisher (KF) coulometer. Solid samples (~5-10 mg) are weighted into a weighing funnel that is used to transfer the material into a titration vessel. To limit the exposure of the solution to the air, the titrator opening is closed by a stopper immediately after adding samples. The sample is mixed for 30 seconds prior to analysis.

In one embodiment, Form A of fedratinib diHCl is prepared by reactive crystallization of fedratinib free base with HCl in THF, acetone or 1,4-dioxane. In a particular embodiment, Form A of fedratinib diHCl is prepared by:
a) dissolving fedratinib free base in a solvent selected from tetrahydrofuran, acetone and 1,4-dioxane at an elevated temperature to form a solution;
b) dissolving HCl in a solvent selected from tetrahydrofuran, acetone and 1,4-dioxane at room temperature to form a solution, wherein the molar equivalent of fedratinib free base to HCl is about 1:2;
c) mixing the solution of step a) and the solution of step b) to form a combined solution;
d) stirring the combined solution of step c) at room temperature overnight to yield Form A of fedratinib diHCl.

In one embodiment, the ratio of fedratinib free base to acetone is less than about 147 mg:1 mL at 45° C. In a particular embodiment, the ratio of fedratinib free base to acetone is about 100 mg:0.8 mL at 65° C. In one embodiment, the ratio of fedratinib free base to THF is about 100 mg:0.6 mL-100 mg:0.2 mL at 45° C. In a particular embodiment, the ratio of fedratinib free base to THF is about 100 mg:0.4 mL at 65° C. In one embodiment, the ratio of fedratinib free base to 1,4-dioxane is less than 100 mg:1 mL at 45° C. In a particular embodiment, the ratio of fedratinib free base to dioxane is about 100 mg:1 mL at 65° C. In one embodiment, the fedratinib free base is dissolved in the solvent to form a clear solution. In one embodiment, the elevated temperature is about 30-80° C. In another embodiment, the elevated temperature is about 40-80° C. In a particular embodiment, the elevated temperature is about 65° C. It will be apparent to one of skill in the art that if the fedratinib free base is not dissolved in the amount of solvent used, more solvent can be added or the suspension can be heated to a higher temperature to obtain a solution. It is advisable that the suspension is not heated above about 80° C. In one embodiment, the HCl is dissolved in the solvent to form a clear solution. In one embodiment, the stirring occurs for about 15 hours. In one embodiment, the fedratinib free base and HCl are both dissolved in tetrahydrofuran. In another embodiment, the fedratinib free base and HCl are both dissolved in acetone. In another embodiment, the fedratinib free base and HCl are both dissolved in 1,4-dioxane. In one embodiment, the HCl is 37% HCl. In another embodiment, the process further comprises vacuum filtering to isolate Form A of fedratinib diHCl.

In another embodiment, Form A of fedratinib diHCl is retained by producing a slurry. In a particular embodiment, Form A of fedratinib diHCl is retained by:
a) combining Form A of fedratinib diHCl with a solvent selected from the group consisting of water, ethanol, methyl tert-butyl ether (MTBE), isopropyl alcohol (IPA), isopropyl acetate (IPAc), 3-methyl-1-butanol, toluene, anisole, acetone, tetrahydrofuran (THF), methyl ethyl ketone (MEK), methyl isobutyl ketone (MIBK), dichloromethane (DCM), 1,4-dioxane, 2-butanol, 2-methyl THF, isobutyl acetate, tert-butanol, methyl cyclohexane, cyclopentyl methyl ether (CPME), or a mixture thereof to form a slurry; and
b) stirring the slurry for about 3 days at room temperature whereby Form A of fedratinib diHCl is retained.

In one embodiment, the ratio of Form A of fedratinib diHCl to solvent is about 30 mg:0.1 mL-30 mg:0.5 mL. In a particular embodiment, the ratio of Form A of fedratinib diHCl to solvent is about 30 mg:0.2 mL. If a solution is formed, more Form A of fedratinib diHCl can be added to form a slurry. In one embodiment, the slurry is centrifuged or filtered to isolate Form A of fedratinib diHCl.

In one embodiment, Form B of fedratinib diHCl is prepared by producing a slurry. In a particular embodiment, Form B of fedratinib diHCl is prepared by:
a) combining Form A of fedratinib diHCl with methanol to form a slurry; and
b) stirring the slurry for about 2 days at room temperature to yield Form B of fedratinib diHCl.

In one embodiment, the ratio of Form A of fedratinib diHCl to methanol is more than 69 mg:1 mL. In a particular embodiment, the ratio of Form A of fedratinib diHCl to methanol is about 53 mg:0.3 mL. In one embodiment, the slurry is centrifuged or filtered to isolate Form B of fedratinib diHCl.

In another embodiment, Form B of fedratinib diHCl is prepared by solvent/anti-solvent addition. In a particular embodiment, Form B of fedratinib diHCl is prepared by:
a) dissolving fedratinib diHCl in MeOH to form a fedratinib diHCl/methanol solution;

b) adding about 3-5 volumes of n-heptane to the fedratinib diHCl/methanol solution dropwise to form a solvent/anti-solvent mixture; and c) stirring the mixture at about −20° C. to about 10° C. for about 4-48 hours to yield Form B of fedratinib diHCl.

In one embodiment, the ratio of fedratinib diHCl to MeOH is less than 69 mg:1 mL at room temperature. In a particular embodiment, the ratio of fedratinib diHCl to MeOH is about 231 mg:1 mL at 50° C. In one embodiment, the fedratinib diHCl is dissolved in MeOH at room temperature. If the fedratinib diHCl is not dissolved in the amount of solvent used, more solvent can be added, or the suspension can be heated to an elevated temperature. In one embodiment, the elevated temperature is about 30-80° C. In another embodiment, the elevated temperature is about 40-80° C. In a particular embodiment, the elevated temperature is about 50° C. In one embodiment, about 4 volumes of n-heptane is added to the fedratinib diHCl/methanol solution. In one embodiment, the stirring is for about 10 hours. In a particular embodiment, the mixture is stirred at about 4° C. In one embodiment, Form B of fedratinib diHCl is isolated by filtration. In another embodiment, Form B of fedratinib diHCl is isolated by centrifugation.

In a further embodiment, Form B of fedratinib diHCl is prepared by temperature cycling. In a particular embodiment, Form B of fedratinib diHCl is prepared by:
a) forming a suspension of Form A of fedratinib diHCl in methanol:cyclohexane (about 1:1, v/v) at about 30-80° C.;
b) cooling the suspension to about 5° C. at a cooling rate of about 0.01-0.2° C./min;
c) heating the suspension to about 30-80° C.;
d) repeating steps b) and c); and
e) maintaining the suspension at about 5° C. to yield Form B of fedratinib diHCl.

In one embodiment, the suspension of Form A of fedratinib diHCl in methanol/cyclohexane is formed at about 40-80° C. In a particular embodiment, the suspension of Form A of fedratinib diHCl in methanol/cyclohexane is formed at about 70° C. In one embodiment, the cooling rate is about 0.1° C./min. In one embodiment, the suspension of step c) is heated to about 40-80° C. In a particular embodiment, the suspension of step c) is heated to about 70° C. In one embodiment, the heating rate is about 5-10° C./min. In a particular embodiment, the heating rate is about 5° C./min. If the heating rate exceeds about 5-10° C./min, it may be necessary to maintain the suspension at an elevated temperature for a period of time to ensure that the entire suspension has reached the desired temperature. In one embodiment, Form B of fedratinib diHCl is isolated by filtration. In another embodiment, Form B of fedratinib diHCl is isolated by centrifugation.

In one embodiment, Form C of fedratinib diHCl is prepared by temperature cycling. In a particular embodiment, Form C of fedratinib diHCl is prepared by:
a) forming a suspension of Form A of fedratinib diHCl in DMF:tert-butanol (about 1:1, v/v) at about 30-80° C.;
b) cooling the suspension to about 5° C. at a cooling rate of about 0.01-0.2° C./min;
c) heating the suspension to about 30-80° C.;
d) repeating steps b) and c); and
e) maintaining the suspension at about 5° C. to yield Form C of fedratinib diHCl.

In one embodiment, the suspension of Form A of fedratinib diHCl in DMF/tert-butanol is formed at about 40-80° C. In a particular embodiment, the suspension of Form A of fedratinib diHCl in DMF/tert-butanol is formed at about 70° C. In one embodiment, the cooling rate is about 0.1° C./min. In one embodiment, the suspension of step c) is heated to about 40-80° C. In a particular embodiment, the suspension of step c) is heated to about 70° C. In one embodiment, the heating rate is about 5-10° C./min. In a particular embodiment, the heating rate is about 5° C./min. If the heating rate exceeds about 5-10° C./min, it may be necessary to maintain the suspension at an elevated temperature for a period of time to ensure that the entire suspension has reached the desired temperature. In one embodiment, Form C of fedratinib diHCl is isolated by filtration. In another embodiment, Form C of fedratinib diHCl is isolated by centrifugation.

In one embodiment, Form D of fedratinib diHCl is prepared by solvent/antisolvent addition. In a particular embodiment, Form D of fedratinib diHCl is prepared by:
a) dissolving fedratinib diHCl in acetic acid to form a fedratinib diHCl/acetic acid solution;
b) adding about 3-5 volumes of isopropyl alcohol dropwise to the fedratinib diHCl/acetic acid solution to form a solvent/antisolvent mixture;
c) stirring the mixture at about 4-10° C. for about 4-48 hours to yield Form D of fedratinib diHCl.

In one embodiment, the ratio of fedratinib diHCl to acetic acid is less than 300 mg:1 mL at room temperature. In a particular embodiment, the ratio of fedratinib diHCl to acetic acid is about 31 mg:0.2 mL at room temperature. If all of the fedratinib diHCl is not dissolved in the acetic acid (i.e., a clear solution is not obtained), the sample can be heated to no higher than about 40° C. to obtain a clear solution. In one embodiment, about 4 volumes of isopropyl alcohol is added to the fedratinib diHCl/acetic acid solution. In a particular embodiment, the mixture is stirred at about 5° C. In one embodiment, the mixture is stirred for about 10 hours. In one embodiment, Form D of fedratinib diHCl is isolated by filtration. In another embodiment, Form D of fedratinib diHCl is isolated by centrifugation.

In another embodiment, Form D of fedratinib diHCl is prepared by slow evaporation. In a particular embodiment, Form D of fedratinib diHCl is prepared by:
a) dissolving fedratinib diHCl in acetic acid at room temperature to form a fedratinib diHCl/acetic acid solution;
b) slow evaporating the fedratinib diHCl/acetic acid solution to yield Form D of fedratinib diHCl.

In one embodiment, the ratio of fedratinib diHCl to acetic acid is less than 300 mg:1 mL at room temperature. In a particular embodiment, the ratio of fedratinib diHCl to acetic acid is about 31 mg:0.2 mL at room temperature. If all of the fedratinib diHCl is not dissolved in the acetic acid (i.e., a clear solution is not obtained), the sample can be heated to no higher than about 40° C. to obtain a clear solution. In one embodiment, slow evaporation is carried out by covering a container with parafilm; making holes in the parafilm; and leaving the covered container under a fume hood until the solvent dries out or until a solid appears. In another embodiment, slow evaporation is carried out by loosely covering a container (e.g., a tube) with a cap and allowing the solvent to evaporate. Slow evaporation can be carried out by any means known to one of ordinary skill in the art.

In one embodiment, Form E of fedratinib diHCl is prepared by producing a slurry. In a particular embodiment, Form E of fedratinib diHCl is prepared by:
a) combining Form A of fedratinib diHCl with dimethylacetamide to form a slurry; and
b) stirring the slurry for about 3 days at room temperature to yield Form E of fedratinib diHCl.

In one embodiment, the ratio of Form A of fedratinib diHCl to dimethylacetamide is more than 50 mg:1 mL. In a particular embodiment, the ratio of Form A of fedratinib diHCl to dimethylacetamide is about 30 mg:0.2 mL. In one embodiment, the slurry is centrifuged or filtered to isolate Form E of fedratinib diHCl.

In one embodiment, Form F of fedratinib diHCl is prepared by producing a slurry. In a particular embodiment, Form F of fedratinib diHCl is prepared by:
 a) combining Form A of fedratinib diHCl with acetonitrile to form a slurry; and
 b) stirring the slurry for about 3 days at room temperature to yield Form F of fedratinib diHCl.

In one embodiment, the ratio of Form A of fedratinib diHCl to acetonitrile is more than 3 mg:1 mL. In a particular embodiment, the ratio of Form A of fedratinib diHCl to acetonitrile is about 32 mg:0.2 mL. In one embodiment, the slurry is centrifuged or filtered to isolate Form F of fedratinib diHCl.

In one embodiment, amorphous fedratinib diHCl is prepared by:
 a) heating Form A of fedratinib diHCl to about 190° C.; or
 b) heating Form F of fedratinib diHCl to about 150° C.; or
 c) heating Form E of fedratinib diHCl to about 160° C., wherein the heating is carried out at a heating rate of about 5-20° C./minute and wherein steps a), b), and c) yield amorphous fedratinib diHCl.

In a particular embodiment, the heating is carried out at a heating rate of about 10° C./min. In one embodiment, an isotherm step can be applied at the final temperature for about 20-40 minutes to ensure that the entire sample has reached the desired temperature.

In one embodiment, the heating is carried out by DSC. In another embodiment, the heating is carried out by TGA. The heating may be carried out by any other method known to those of skill in the art.

In another embodiment, amorphous fedratinib diHCl is prepared by:
 a) subjecting Form A of fedratinib diHCl to a dynamic vapor sorption method to yield amorphous fedratinib diHCl, wherein the dynamic vapor sorption method comprises exposing the Form A of fedratinib diHCl to a relative humidity of about 50% and adjusting the relative humidity to between about 0-90% with about a 10% increase or decrease in humidity at each step for 3 cycles.

In one embodiment, a fedratinib diHCl co-crystal with succinic acid is prepared by:
 a) suspending Form A of fedratinib diHCl in MeOH:acetone (about 1:2, v/v) at room temperature;
 b) suspending succinic acid in MeOH:acetone (about 1:2, v/v) at room temperature;
 c) mixing the Form A fedratinib diHCl/MeOH/acetone suspension of step a) with the succinic acid/MeOH/acetone suspension of step b) to form a mixture;
 d) stirring the mixture at room temperature for about 6-48 hours;
 e) cooling the mixture to about 4° C. at a cooling rate of about 0.01-0.2° C./min to yield a fedratinib diHCl co-crystal with succinic acid.

In one embodiment, the ratio of Form A of fedratinib diHCl to MeOH/acetone is more than 23 mg:1 mL. In a particular embodiment, the ratio of Form A of fedratinib diHCl to MeOH/acetone is about 30 mg:0.15 mL. In one embodiment, the ratio of succinic acid to MeOH/acetone is about 5.9 mg:0.03 mL. In one embodiment, the ratio of Form A of fedratinib diHCl to MeOH/acetone and the ratio of succinic acid to MeOH/acetone are such that the solubility of Form A of fedratinib diHCl in MeOH/acetone is similar to the solubility of succinic acid in MeOH/acetone. In a particular embodiment, the molar ratio of Form A of fedratinib diHCl to succinic acid is about 1:1. In one embodiment, the mixture is stirred for about 6 hours. In a particular embodiment, the cooling rate is about 0.1° C./min.

In one embodiment, a fedratinib diHCl co-crystal with fumaric acid is prepared by:
 a) suspending Form A of fedratinib diHCl in MeOH:acetone (about 1:2, v/v) at room temperature;
 b) suspending fumaric acid in MeOH:acetone (about 1:2, v/v) at room temperature;
 c) mixing the Form A fedratinib diHCl/MeOH/acetone suspension of step a) with the fumaric acid/MeOH/acetone suspension of step b) to form a mixture;
 d) stirring the mixture at room temperature for about 6-48 hours;
 e) cooling the mixture to about 4° C. at a cooling rate of about 0.01-0.2° C./min to yield a fedratinib diHCl co-crystal with fumaric acid.

In one embodiment, the ratio of Form A of fedratinib diHCl to MeOH/acetone is more than 23 mg:1 mL. In a particular embodiment, the ratio of Form A of fedratinib diHCl to MeOH/acetone is about 30 mg:0.15 mL. In a particular embodiment, the ratio of fumaric acid to MeOH/acetone is about 5.8 mg:0.03 mL. In one embodiment, the ratio of Form A of fedratinib diHCl to MeOH/acetone and the ratio of fumaric acid to MeOH/acetone are such that the solubility of Form A of fedratinib diHCl in MeOH/acetone is similar to the solubility of fumaric acid in MeOH/acetone. In a particular embodiment, the molar ratio of Form A of fedratinib diHCl to fumaric acid is about 1:1. In one embodiment, the mixture is stirred for about 6 hours. In a particular embodiment, the cooling rate is about 0.1° C./min.

In one embodiment, a fedratinib diHCl co-crystal with sucrose is prepared by:
 a) suspending Form A of fedratinib diHCl in MeOH:acetone (about 1:2, v/v) at room temperature;
 b) suspending sucrose in MeOH:acetone (about 1:2, v/v) at room temperature; c) mixing the Form A fedratinib diHCl/MeOH/acetone suspension of step a) with the sucrose/MeOH/acetone suspension of step b) to form a mixture;
 d) stirring the mixture at room temperature for about 6-48 hours;
 e) cooling the mixture to about 4° C. at a cooling rate of about 0.01-0.2° C./min to yield a fedratinib diHCl co-crystal with sucrose.

In one embodiment, the ratio of Form A of fedratinib diHCl to MeOH/acetone is more than about 23 mg:1 mL. In a particular embodiment, the ratio of Form A of fedratinib diHCl to MeOH/acetone is about 30 mg:0.15 mL. In one embodiment, the ratio of sucrose to MeOH/acetone is about 17 mg:0.03 mL. In one embodiment, the ratio of Form A of fedratinib diHCl to MeOH/acetone and the ratio of sucrose to MeOH/acetone are such that the solubility of Form A of fedratinib diHCl in MeOH/acetone is similar to the solubility of sucrose in MeOH/acetone. In a particular embodiment, the molar ratio of Form A of fedratinib diHCl to sucrose is about 1:1. In one embodiment, the mixture is stirred for about 6 hours. In a particular embodiment, the cooling rate is about 0.1° C./min.

The present disclosure also encompasses a pharmaceutical composition comprising one of Forms A-F of fedratinib diHCl, amorphous fedratinib diHCl, a fedratinib diHCl co-crystal with succinic acid, a fedratinib diHCl co-crystal with fumaric acid, and a fedratinib diHCl co-crystal with sucrose and a pharmaceutically acceptable excipient. A pharmaceutical composition containing fedratinib diHCl may be prepared according to U.S. Pat. No. 10,391,094, or any other methods known in the art.

The present disclosure provides for a method of treating disease by administering to a patient, in need thereof, a pharmaceutical composition comprising one of Forms A-F of fedratinib diHCl, amorphous fedratinib diHCl, a fedratinib diHCl co-crystal with succinic acid, a fedratinib diHCl co-crystal with fumaric acid, and a fedratinib diHCl co-crystal with sucrose. Fedratinib diHCl is indicated for the treatment of a patient with myelofibrosis. It may be used in combination with another pharmaceutically acceptable agent, for example, luspatercept.

Inrebic® (fedratinib) capsules are available in a 100 mg unit dosage. The recommended dosage is 400 mg orally once daily with or without food for patients with a baseline platelet count of greater than or equal to $50 \times 10^9$/L. The dosage is reduced for patients taking strong CYP3A inhibitors or with severe renal impairment.

EXAMPLES

The Examples are presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are illustrative of the present disclosure and the disclosure is not intended to be limited to the examples described herein and shown.

Example 1—Preparation of Form a of Fedratinib diHCl

Fedratinib diHCl is generated by reactive crystallization of fedratinib free base (1 equivalent) with HCl (2 equivalents) in acetone. Specifically, 100 mg (0.19 mole) of fedratinib free base is dissolved in 0.8 mL of acetone at 65° C. 37.6 mg (0.38 mole) of 37% HCl is dissolved in 0.02 mL of acetone at 20° C. The two solutions are mixed together and stirred at 20° C. overnight (~15 hours). The solid is obtained by vacuum filtration and analyzed by XRPD as Form A of fedratinib diHCl.

Form A of fedratinib diHCl is characterized by its XRPD pattern peaks. 2Θ and relative % intensity values for peaks are shown in Table 1.

TABLE 1

Average Peak List for Form A of fedratinib diHCl

| Angle 2-Theta ° | Intensity % % |
|---|---|
| 7.0 | 18.8 |
| 9.3 | 52.9 |
| 9.6 | 14.2 |
| 10.0 | 14.7 |
| 11.2 | 28.2 |
| 12.0 | 30.9 |

TABLE 1-continued

Average Peak List for Form A of fedratinib diHCl

| Angle 2-Theta ° | Intensity % % |
|---|---|
| 12.5 | 13.1 |
| 13.2 | 51.9 |
| 14.0 | 16.3 |
| 14.3 | 18.6 |
| 14.7 | 21.4 |
| 15.1 | 13.7 |
| 15.3 | 13.9 |
| 15.7 | 26.7 |
| 15.9 | 62.4 |
| 16.7 | 100 |
| 17.3 | 39.3 |
| 17.8 | 45.7 |
| 18.1 | 14.5 |
| 18.3 | 17.7 |
| 18.9 | 26.8 |
| 19.8 | 24.4 |
| 20.8 | 18.3 |
| 21.0 | 11.9 |
| 21.5 | 33.8 |
| 23.4 | 18.9 |
| 23.8 | 42.6 |
| 25.0 | 15.1 |
| 26.6 | 14.2 |
| 26.9 | 17.7 |
| 27.4 | 19.8 |
| 34.0 | 17.2 |
| 35.6 | 10.7 |
| 36.0 | 12 |
| 38.2 | 10 |

The angle measurements are ±0.2° 2Θ. In one embodiment, key defining peaks for solid-state Form A of fedratinib diHCl include two or more of 9.3, 15.9, and 16.7° 2Θ.

FIG. 1 is a representative XRPD pattern of Form A of fedratinib diHCl.

Figure 2:
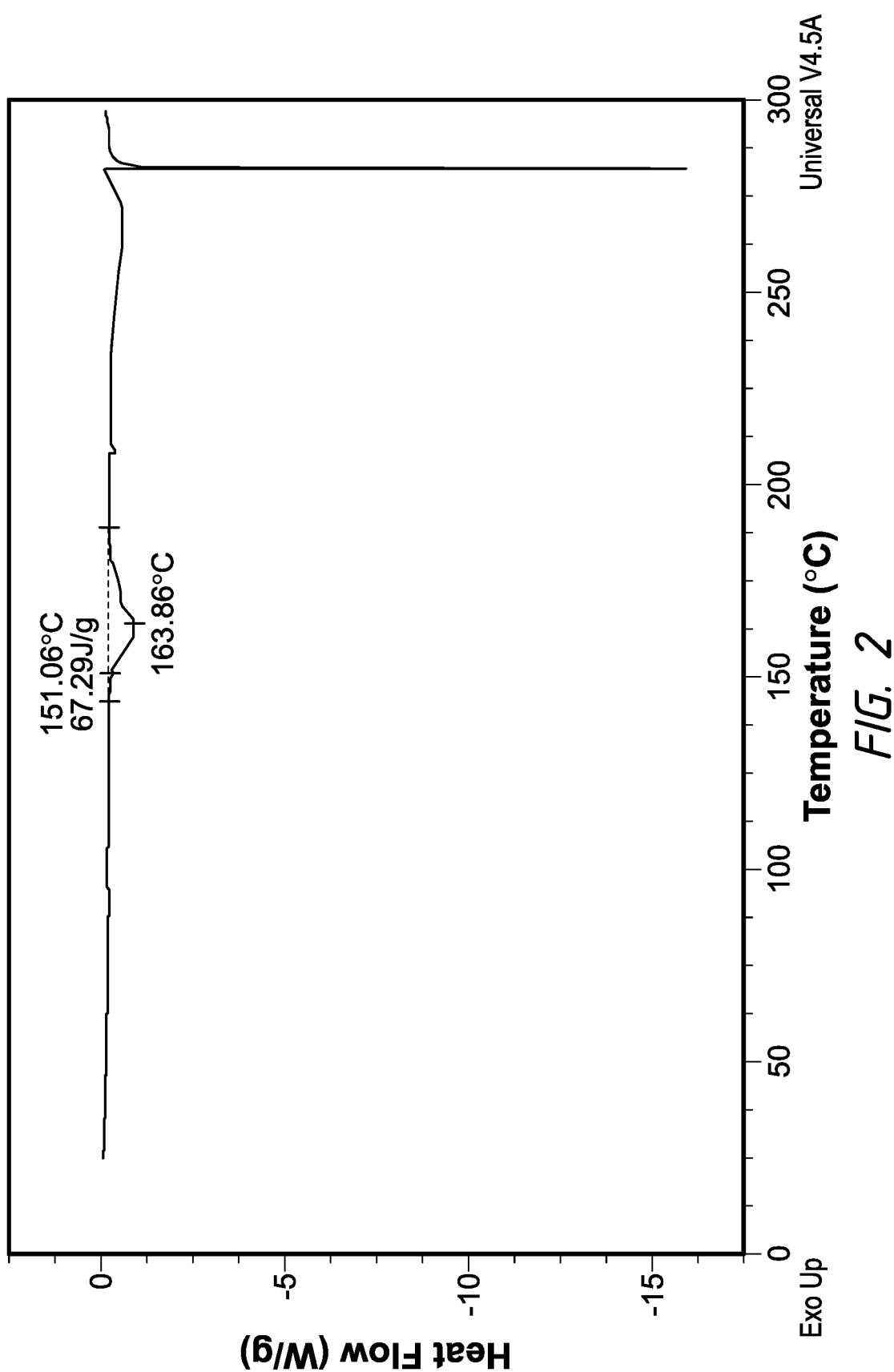
FIG. 2 is a representative DSC of Form A of fedratinib diHCl.

FIG. 2 is a representative DSC of Form A of fedratinib diHCl which shows an endotherm with an onset temperature at about 151° C.

Figure 3:
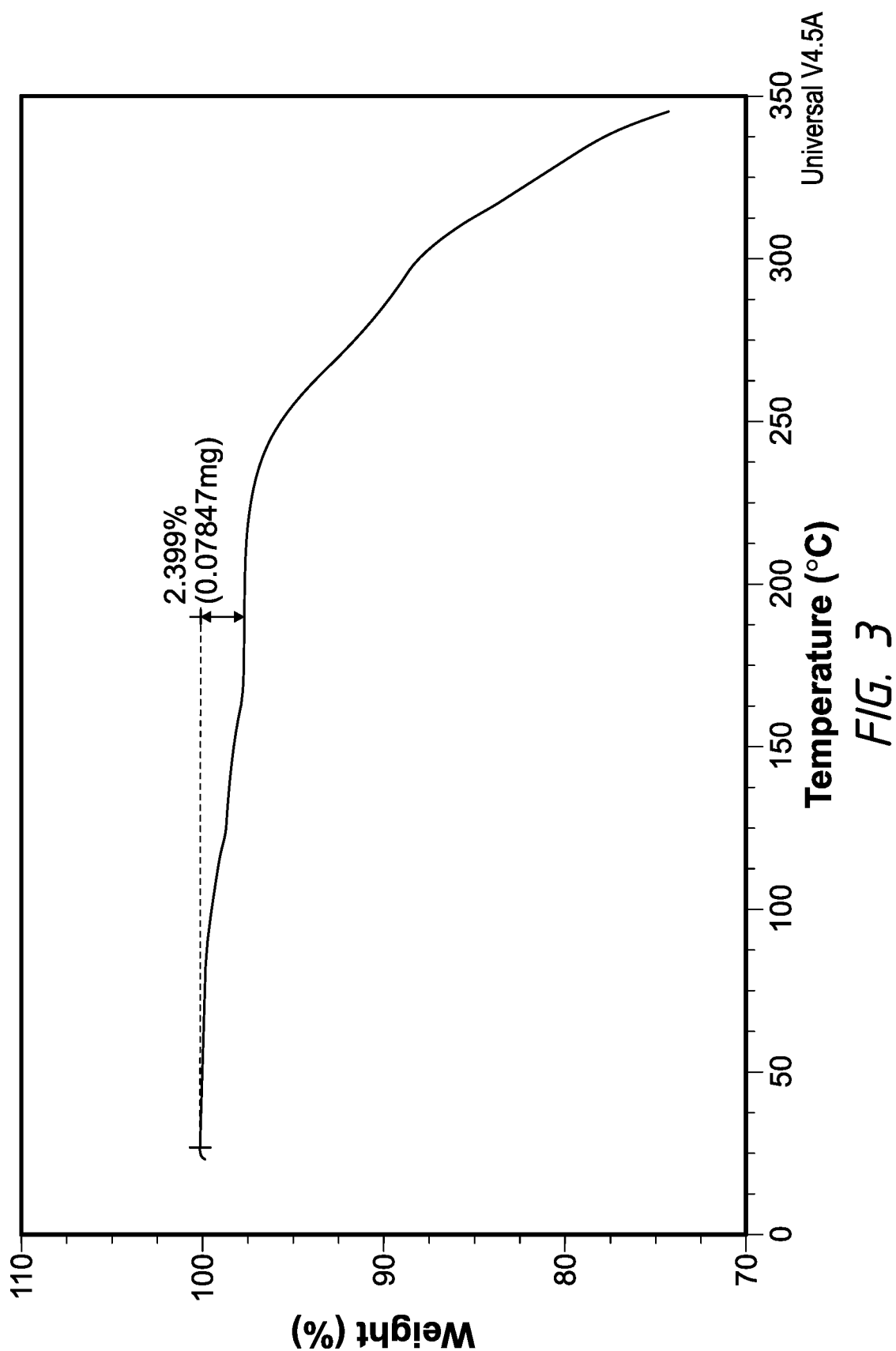
FIG. 3 is a representative TGA of Form A of fedratinib diHCl.

FIG. 3 is a representative TGA of Form A of fedratinib diHCl which shows a weight loss of about 2.4% up to about 190° C.

KF data indicates the presence of about 3.9% water in a sample of Form A of fedratinib diHCl.

Example 2—Preparation of Form A of Fedratinib diHCl

Fedratinib diHCl is generated by reactive crystallization of fedratinib free base (1 equivalent) with HCl (2 equivalents) in THF. Specifically, 100 mg (0.19 mole) of fedratinib free base is dissolved in 0.4 mL of THF at 65° C. 37.6 mg (0.38 mole) of 37% HCl is dissolved in 0.02 mL of THF at 20° C. The two solutions are mixed together and stirred at 20° C. overnight (~15 hours). The solid is obtained by vacuum filtration and analyzed by XRPD as Form A of fedratinib diHCl.

Example 3—Preparation of Form A of Fedratinib diHCl

Fedratinib diHCl is generated by reactive crystallization of fedratinib free base (1 equivalent) with HCl (2 equivalents) in 1,4-dioxane. Specifically, 100 mg (0.19 mole) of fedratinib free base is dissolved in 1.0 mL of 1,4-dioxane at 65° C. 37.6 mg (0.38 mole) of 37% HCl is dissolved in 0.02 mL of 1,4-dioxane at room temperature. The two solutions are mixed together and stirred at 20° C. overnight (~15 hours). The solid is obtained by vacuum filtration and analyzed by XRPD as Form A of fedratinib diHCl.

Example 4—Retention of Form A of Fedratinib diHCl

Form A of fedratinib diHCl is also retained by obtaining a slurry in multiple solvents. Specifically, ~30 mg (0.05 mole) of Form A of fedratinib diHCl is dispersed in 0.2 mL of each of the following solvents: water, ethanol, methyl tert-butyl ether (MTBE), isopropyl alcohol (IPA), isopropyl acetate (IPAc), 3-methyl-1-butanol, toluene, anisole, acetone, tetrahydrofuran (THF), methyl ethyl ketone (MEK), methyl isobutyl ketone (MIBK), dichloromethane (DCM), 1,4-dioxane, 2-butanol, 2-methyl THF, isobutyl acetate, tert-butanol, methyl cyclohexane, cyclopentyl methyl ether (CPME) and is slurried for about 3 days at 20° C. The resulting material is analyzed by XRPD and determined to be Form A of fedratinib diHCl.

Example 5—Preparation of Form B of Fedratinib diHCl 53.2 mg (0.09 mole) of Form A of fedratinib diHCl is dispersed in 0.3 mL of methanol and slurried for 2 days at 20° C. The resulting material is analyzed by XRPD and determined to be Form B of fedratinib diHCl.

Example 6—Preparation of Form B of Fedratinib diHCl 230.5 mg (0.39 mole) of fedratinib diHCl is dissolved in 1 mL of MeOH at 50° C. 0.6 mL (4 volumes) of n-heptane is added to 0.15 mL of the MeOH/fedratinib diHCl solution drop by drop. The sample is stirred at 4° C. for ~10 hours. The resulting precipitate is analyzed by XRPD and determined to be Form B of fedratinib diHCl.

Example 7—Preparation of Form B of Fedratinib diHCl

A suspension of Form A of fedratinib diHCl is prepared in methanol:cyclohexane (1:1, v/v) at 70° C. followed by cooling to 5° C. at the cooling rate of 0.1° C./min. The suspension is then heated up to 70° C. at the heating rate of 5° C./min. This cycle is repeated one more time and the sample is kept at 5° C. prior to solid isolation. The solid is analyzed by XRPD and determined to be Form B of fedratinib diHCl.

Form B of fedratinib diHCl is characterized by its XRPD pattern peaks. 2Θ and relative % intensity values for peaks are shown in Table 2.

TABLE 2

| Average Peak List for Form B of fedratinib diHCl | |
|---|---|
| Angle 2-Theta ° | Intensity % % |
| 9.4 | 30.8 |
| 11.2 | 100 |
| 11.7 | 22.6 |
| 12.3 | 38.4 |
| 12.6 | 31.5 |
| 14.8 | 92.5 |
| 15.7 | 25.3 |
| 16.1 | 19.2 |

TABLE 2-continued

| Average Peak List for Form B of fedratinib diHCl | |
|---|---|
| Angle 2-Theta ° | Intensity % % |
| 17.1 | 21.9 |
| 20.1 | 28.1 |
| 20.8 | 30.8 |
| 22.7 | 28.8 |
| 23.6 | 23.3 |
| 25.1 | 21.9 |

The angle measurements are ±0.2° 2Θ. In one embodiment, key defining peaks for solid-state Form B of fedratinib diHCl include two or more of 11.2, 12.3, and 14.8° 2Θ.

Figure 4:
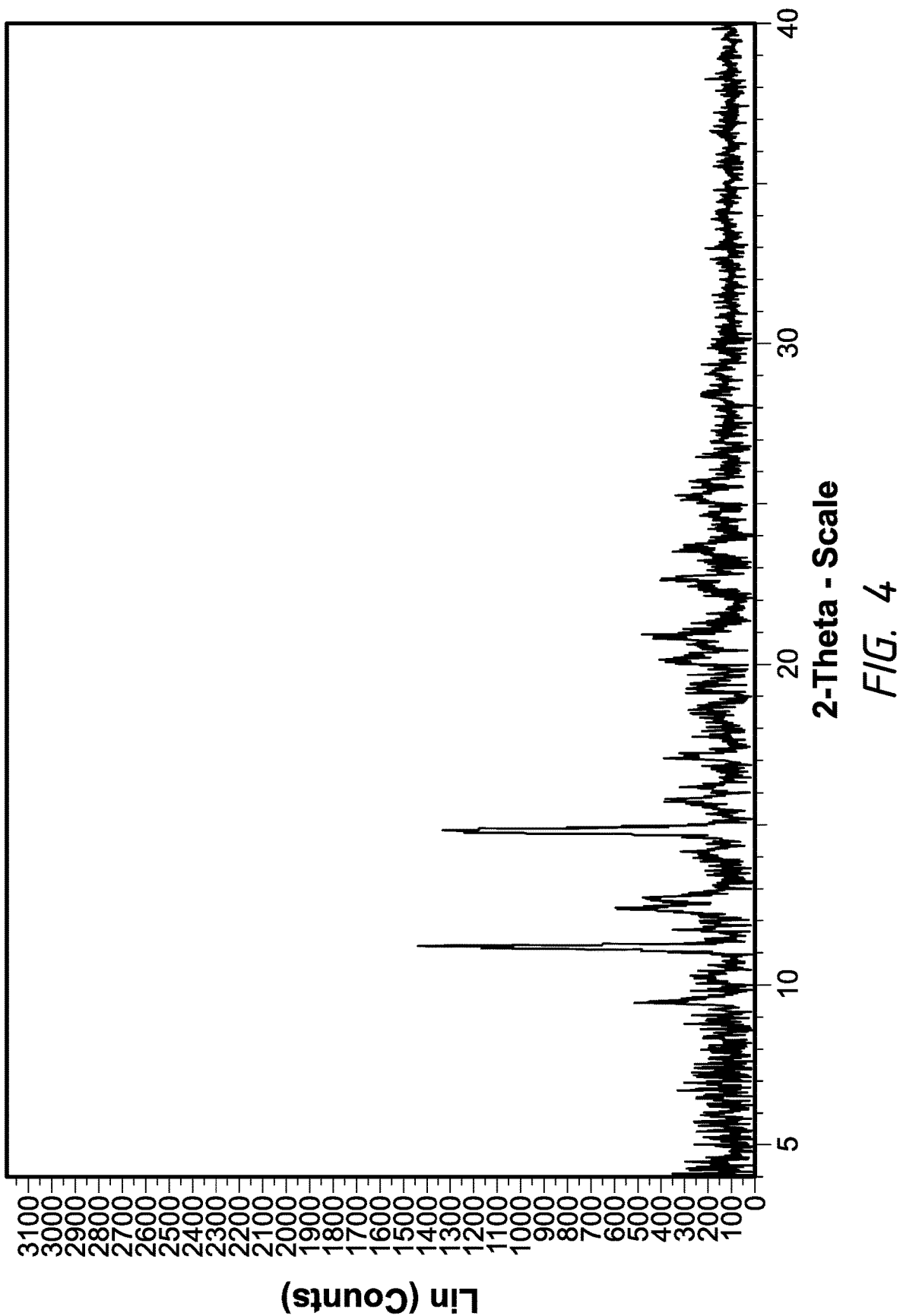
FIG. 4 is a representative XRPD pattern of Form B of fedratinib diHCl.

FIG. 4 is a representative XRPD pattern of Form B of fedratinib diHCl.

Figure 5:
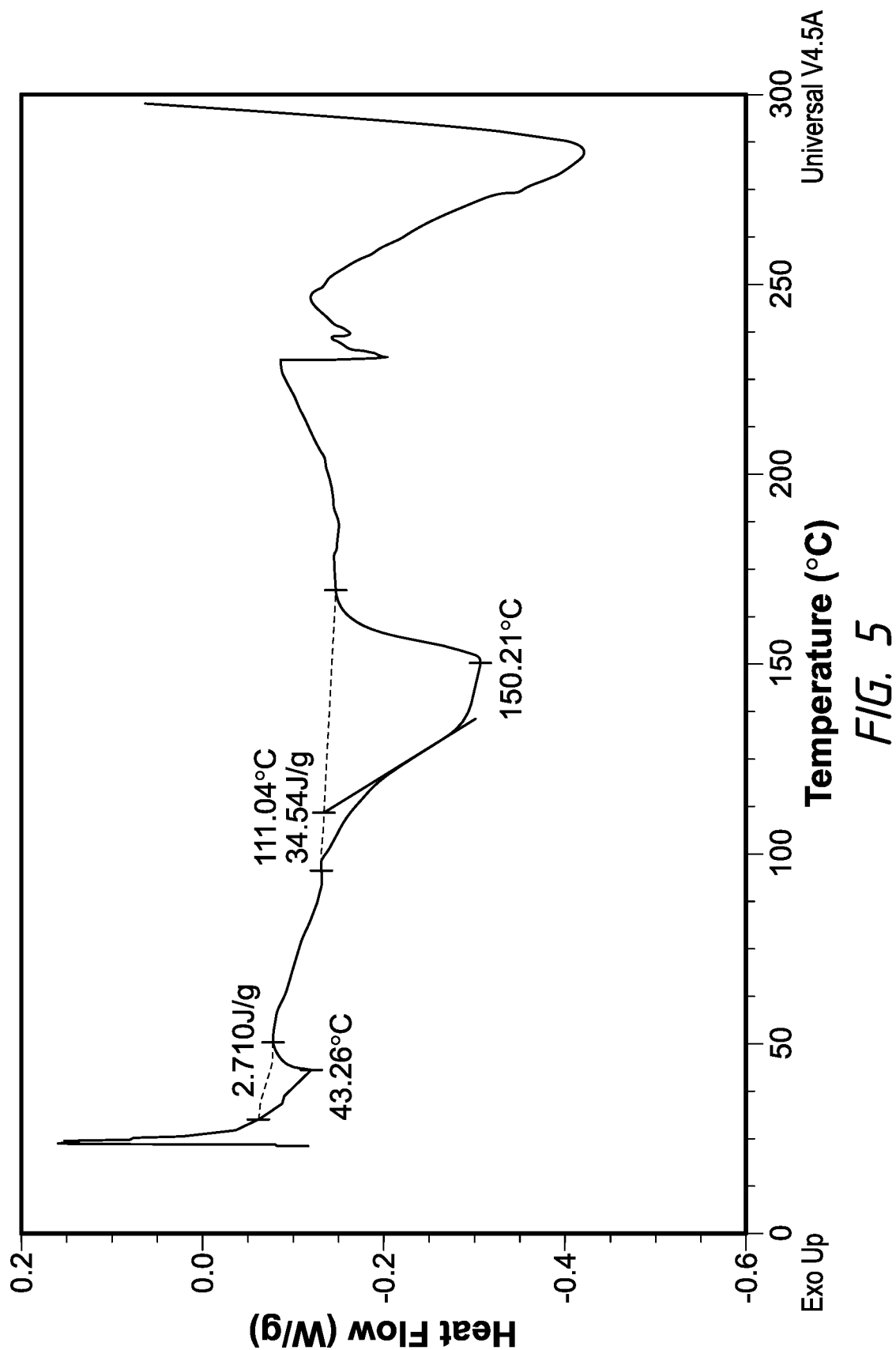
FIG. 5 is a representative DSC of Form B of fedratinib diHCl.

FIG. 5 is a representative DSC of Form B of fedratinib diHCl which shows an endotherm at about 43° C. and an endotherm with an onset temperature at about 111° C.

Figure 6:
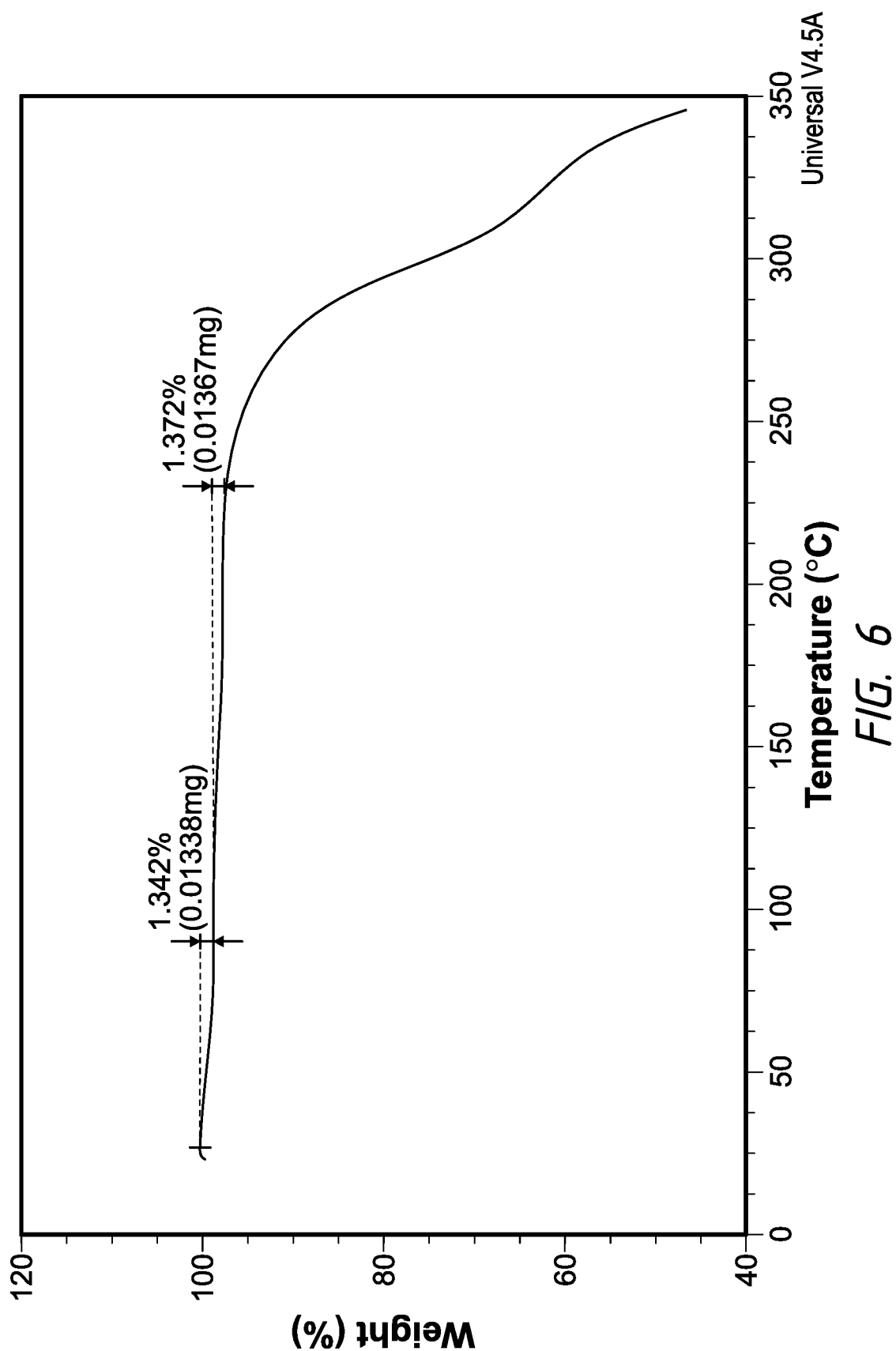
FIG. 6 is a representative TGA of Form B of fedratinib diHCl.

FIG. 6 is a representative TGA of Form B of fedratinib diHCl which shows a weight loss of about 1.3% up to about 90° C. followed by a secondary weight loss of about 1.4%.

No solvent except water is observed by $^1$H NMR. Furthermore, KF data indicates the presence of about 4.5% water in a sample of Form B of fedratinib diHCl.

Example 8—Preparation of Form C of Fedratinib diHCl

A suspension of Form A of fedratinib diHCl is prepared in DMF:tert-butanol (1:1, v/v) at 70° C. followed by cooling to 5° C. at the cooling rate of 0.1° C./min. The suspension is then heated up to 70° C. at the heating rate of 5° C./min. This cycle is repeated one more time and the sample is kept at 5° C. prior to solid isolation. The solid is analyzed by XRPD and determined to be Form C of fedratinib diHCl.

Form C of fedratinib diHCl is characterized by its XRPD pattern peaks. 2Θ and relative % intensity values for peaks are shown in Table 3.

TABLE 3

| Average Peak List for Form C of fedratinib diHCl | |
|---|---|
| Angle 2-Theta ° | Intensity % % |
| 9.4 | 5.2 |
| 9.6 | 8.2 |
| 12.1 | 5.7 |
| 12.4 | 7.1 |
| 12.9 | 5.7 |
| 13.2 | 10.9 |
| 15.4 | 100 |
| 15.7 | 7.1 |
| 16.6 | 58.2 |
| 17.1 | 42.7 |
| 17.3 | 10.2 |
| 17.5 | 3.6 |
| 17.8 | 35.4 |
| 18.3 | 6.1 |
| 20.7 | 59 |
| 21.5 | 13.4 |
| 22.1 | 10.7 |
| 23.3 | 4.8 |
| 23.8 | 7.7 |
| 24.3 | 5.9 |
| 24.6 | 5.2 |
| 25.0 | 5.2 |
| 25.3 | 4 |
| 26.0 | 32.6 |

TABLE 3-continued

Average Peak List for Form C of fedratinib diHCl

| Angle 2-Theta ° | Intensity % |
|---|---|
| 26.9 | 7.7 |
| 27.2 | 9.6 |
| 29.0 | 3.3 |
| 30.0 | 5.6 |
| 31.4 | 7.9 |
| 34.0 | 4.2 |
| 34.9 | 4 |
| 36.0 | 4.6 |
| 38.9 | 5 |

The angle measurements are ±0.2° 2Θ. In one embodiment, key defining peaks for solid-state Form C of fedratinib diHCl include two or more of 15.4, 16.6, and 17.1° 2Θ.

Figure 7:
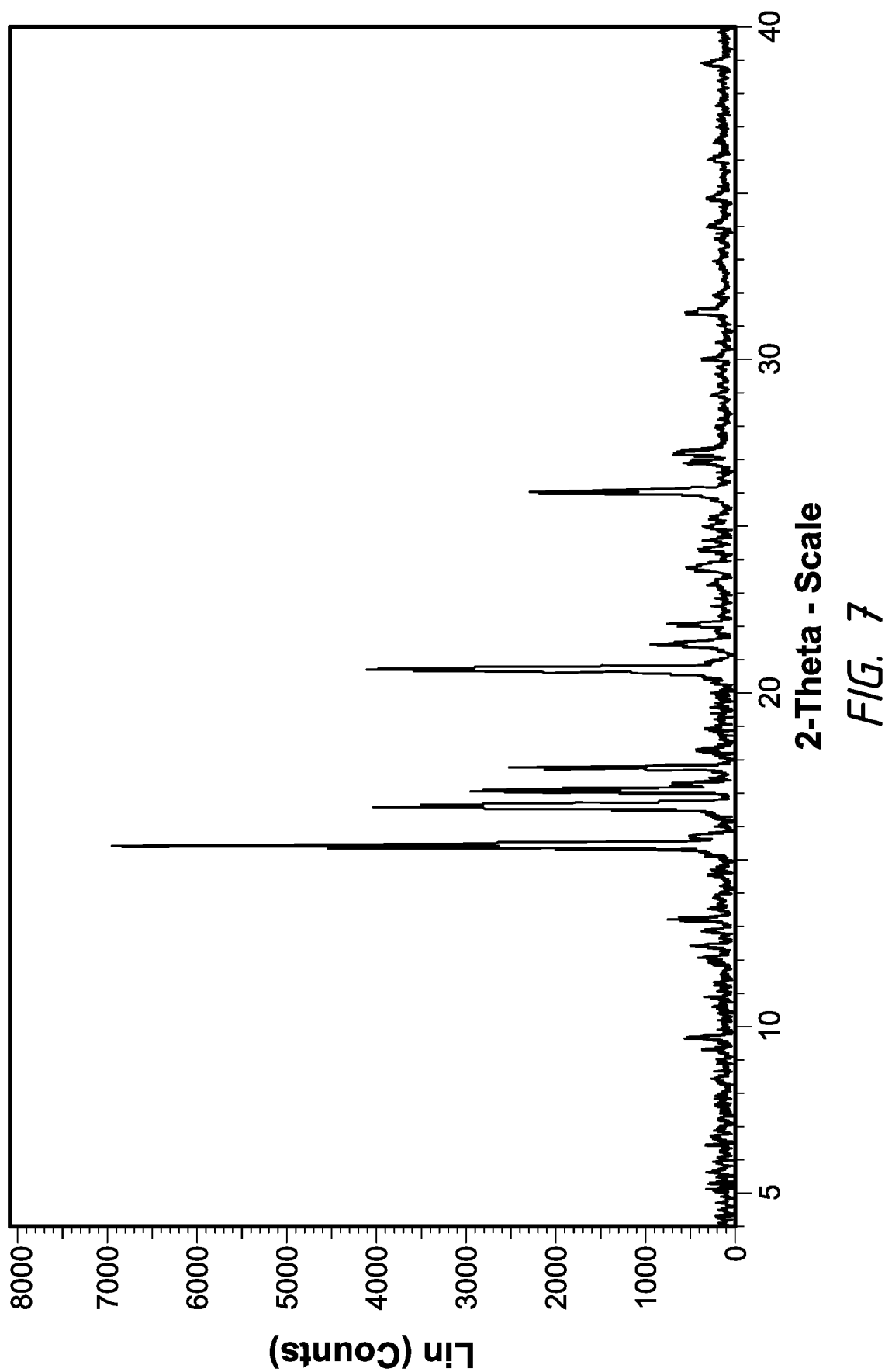
FIG. 7 is a representative XRPD pattern of Form C of fedratinib diHCl.

FIG. 7 is a representative XRPD pattern of Form C of fedratinib diHCl.

Figure 8:
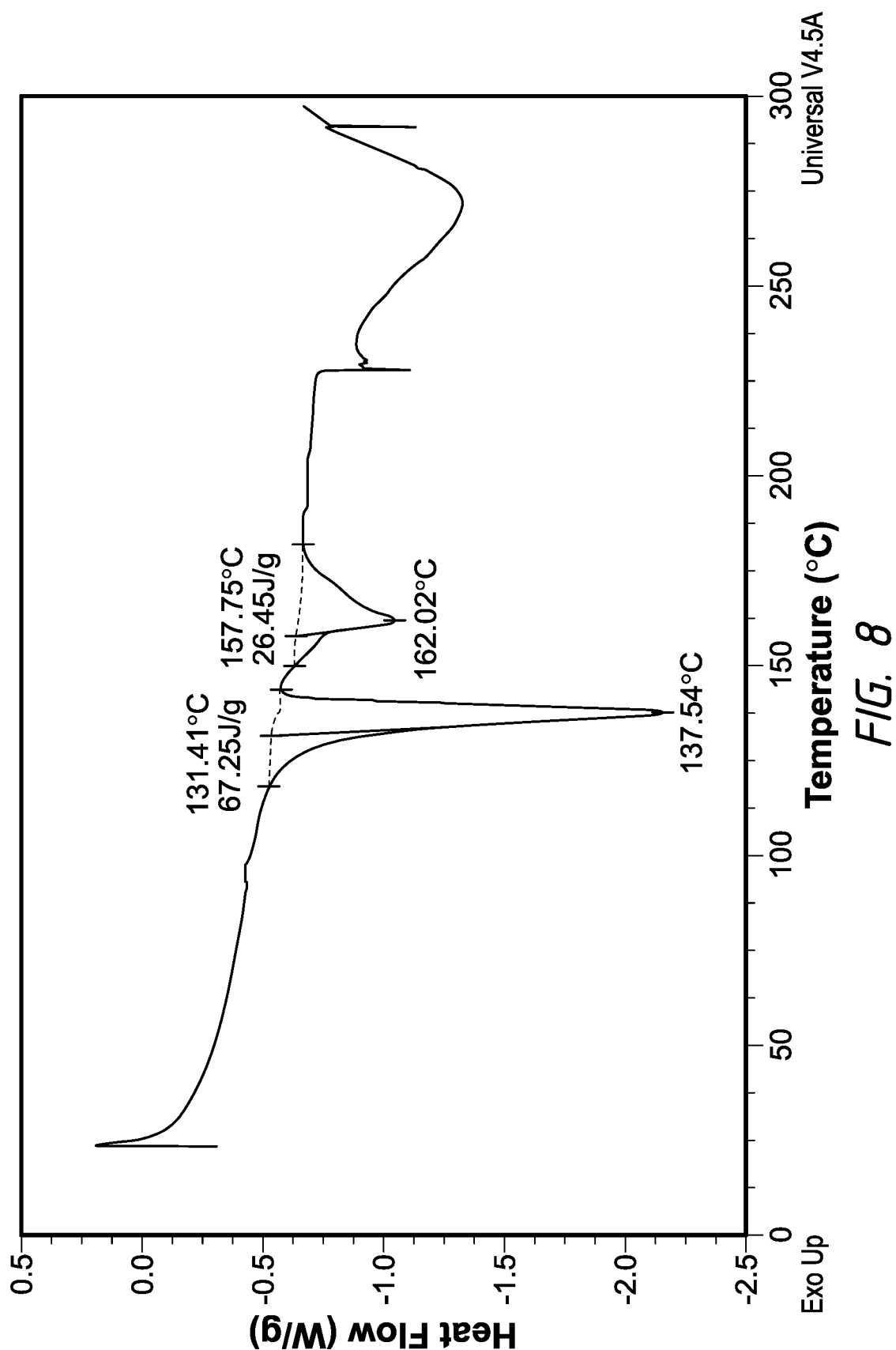
FIG. 8 is a representative DSC of Form C of fedratinib diHCl.

FIG. 8 is a representative DSC of Form C of fedratinib diHCl which shows endotherms with onset temperatures at about 131 and 158° C.

Figure 9:
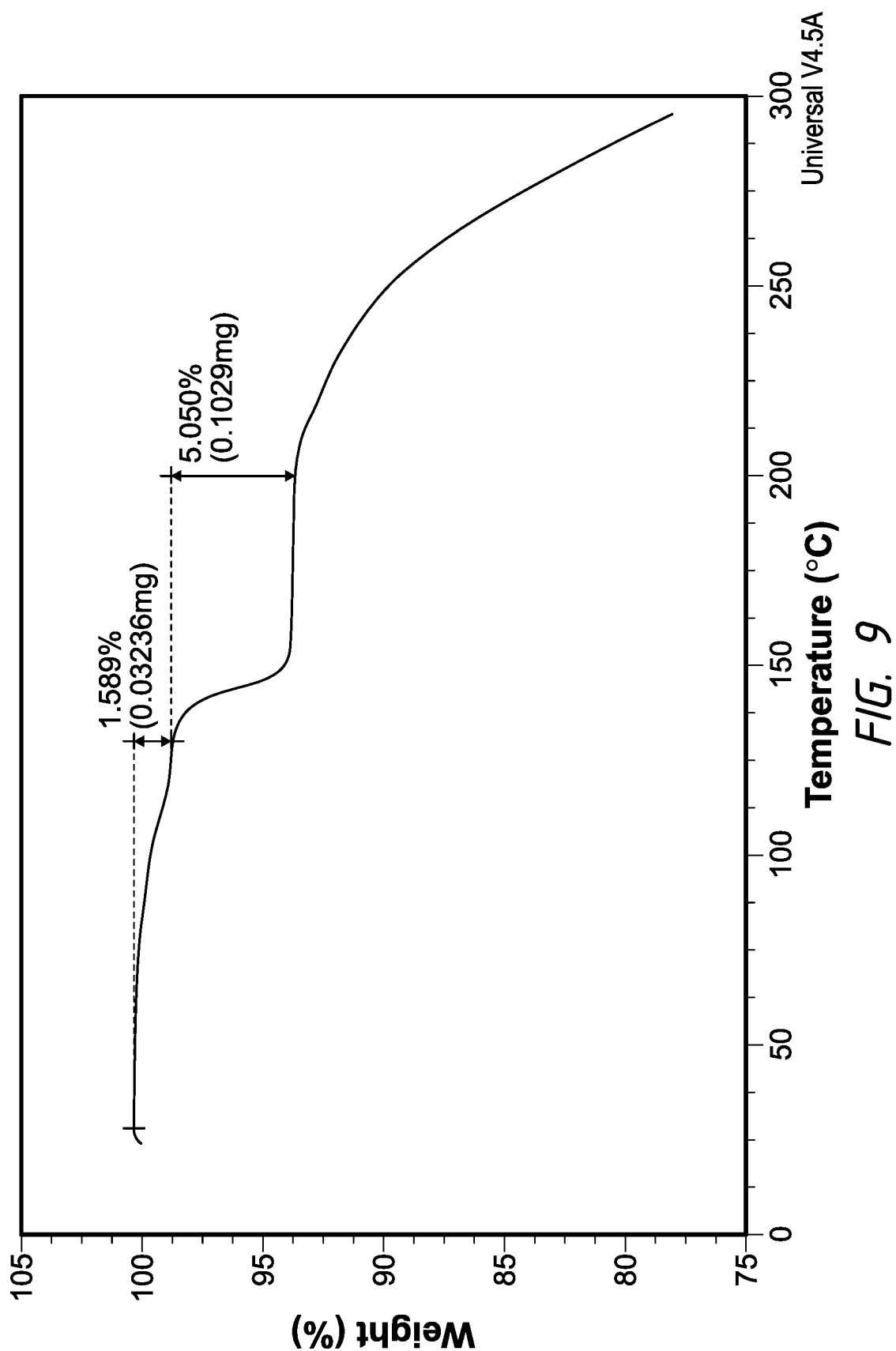
FIG. 9 is a representative TGA of Form C of fedratinib diHCl.

FIG. 9 is a representative TGA of Form C of fedratinib diHCl which shows a weight loss of about 1.6% up to about 130° C. followed by a secondary weight loss of about 5.1%.

Water and residual DMF are observed by ¹H NMR. Furthermore, KF data indicates the presence of about 2.9% water in a sample of Form C of fedratinib diHCl.

Example 9—Preparation of Form D of Fedratinib diHCl 31.3 mg (0.05 mole) of fedratinib diHCl is dissolved in 0.2 mL of acetic acid at 20° C. 0.8 mL (4 volumes) of IPA is added drop by drop to the fedratinib diHCl/acetic acid solution. The clear solution is stirred at 5° C. overnight (~10 hours). The resulting precipitate is analyzed by XRPD and determined to be Form D of fedratinib diHCl.

Example 10—Preparation of Form D of Fedratinib diHCl 31.3 mg (0.05 mole) of fedratinib diHCl is dissolved in 0.2 mL of acetic acid at 20° C. in a glass vial. The acetic acid solution of fedratinib diHCl is subjected to slow evaporation by covering the vial with parafilm, making about 4-6 holes in the parafilm, and placing the covered vial under a fume hood until the solvent evaporates. The resulting solid is analyzed by XRPD and determined to be Form D of fedratinib diHCl.

Form D of fedratinib diHCl is characterized by its XRPD pattern peaks. 2Θ and relative % intensity values for peaks are shown in Table 4.

TABLE 4

Average Peak List for Form D of fedratinib diHCl

| Angle 2-Theta ° | Intensity % |
|---|---|
| 5.2 | 90.8 |
| 5.9 | 36.8 |
| 7.8 | 64 |
| 8.5 | 54 |
| 9.0 | 33.1 |
| 9.2 | 44.8 |
| 9.6 | 44.4 |
| 9.7 | 33.1 |
| 10.1 | 27.2 |
| 10.3 | 35.6 |
| 10.5 | 40.2 |
| 12.4 | 50.6 |
| 13.2 | 34.3 |
| 15.5 | 42.3 |
| 15.7 | 59.8 |
| 15.9 | 72.8 |
| 16.1 | 36 |
| 16.3 | 34.3 |
| 16.7 | 100 |
| 16.9 | 97.5 |
| 17.0 | 35.1 |
| 17.3 | 70.7 |
| 17.7 | 78.7 |
| 18.0 | 38.5 |
| 18.3 | 47.7 |
| 18.9 | 42.3 |
| 20.8 | 68.2 |
| 21.5 | 46.4 |
| 21.7 | 53.1 |
| 24.5 | 37.7 |

The angle measurements are ±0.2° 2Θ. In one embodiment, key defining peaks for solid-state Form D of fedratinib diHCl include two or more of 5.2, 16.7, and 16.9° 2Θ.

Figure 10:
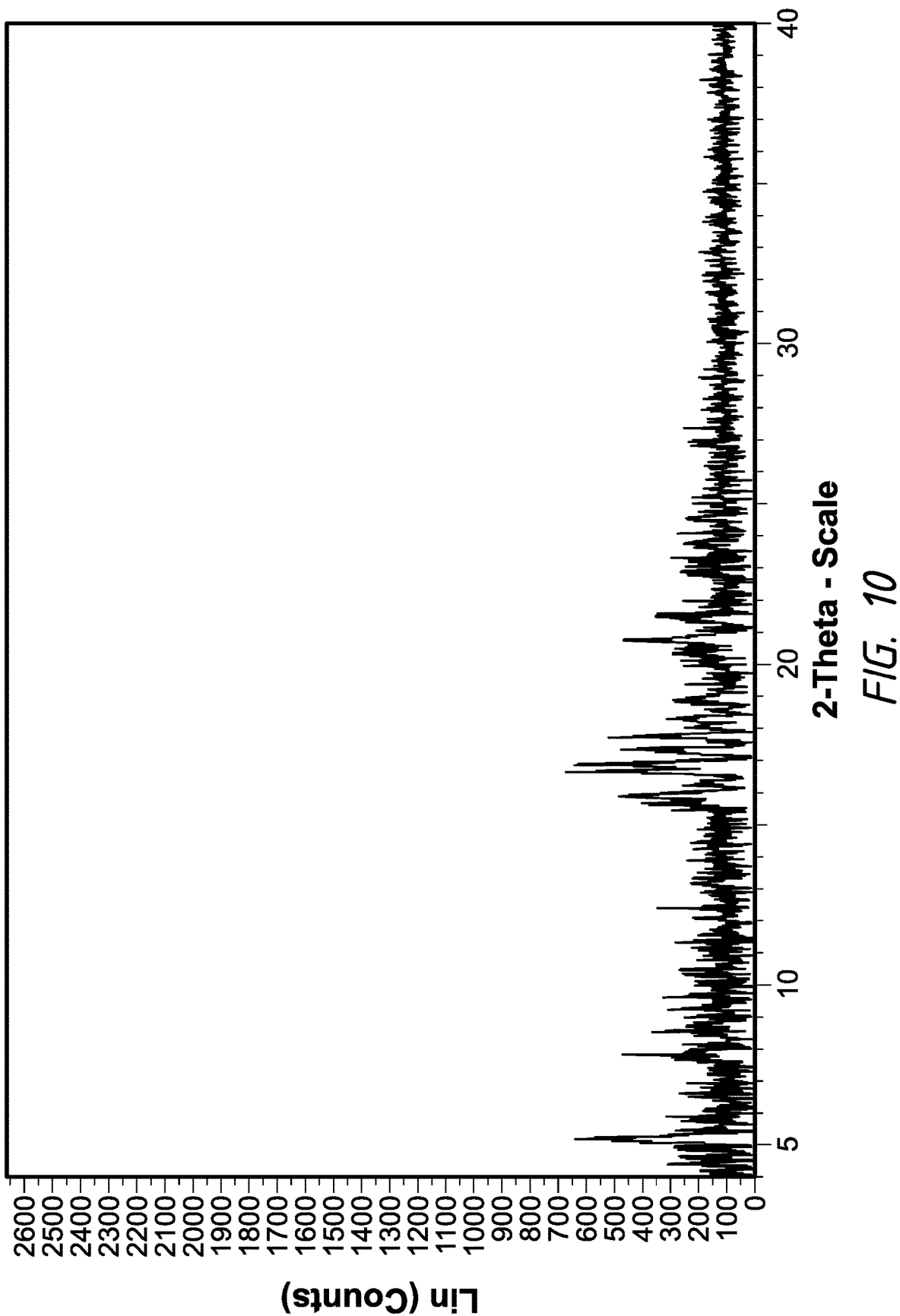
FIG. 10 is a representative XRPD pattern of Form D of fedratinib diHCl.

FIG. 10 is a representative XRPD pattern of Form D of fedratinib diHCl.

Figure 11:
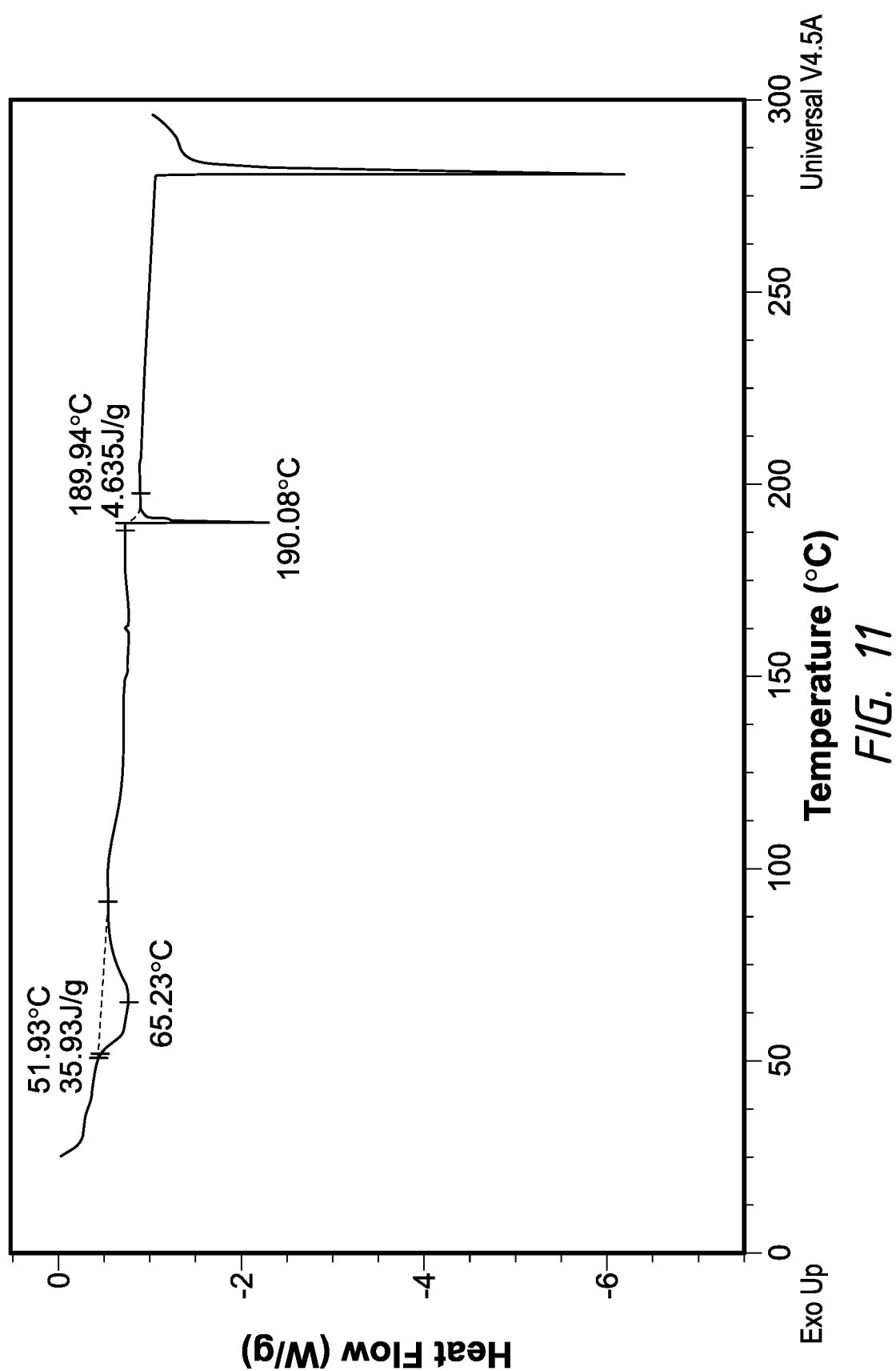
FIG. 11 is a representative DSC of Form D of fedratinib diHCl.

FIG. 11 is a representative DSC of Form D of fedratinib diHCl which shows endotherms with onset temperatures at about 52 and 190° C.

Figure 12:
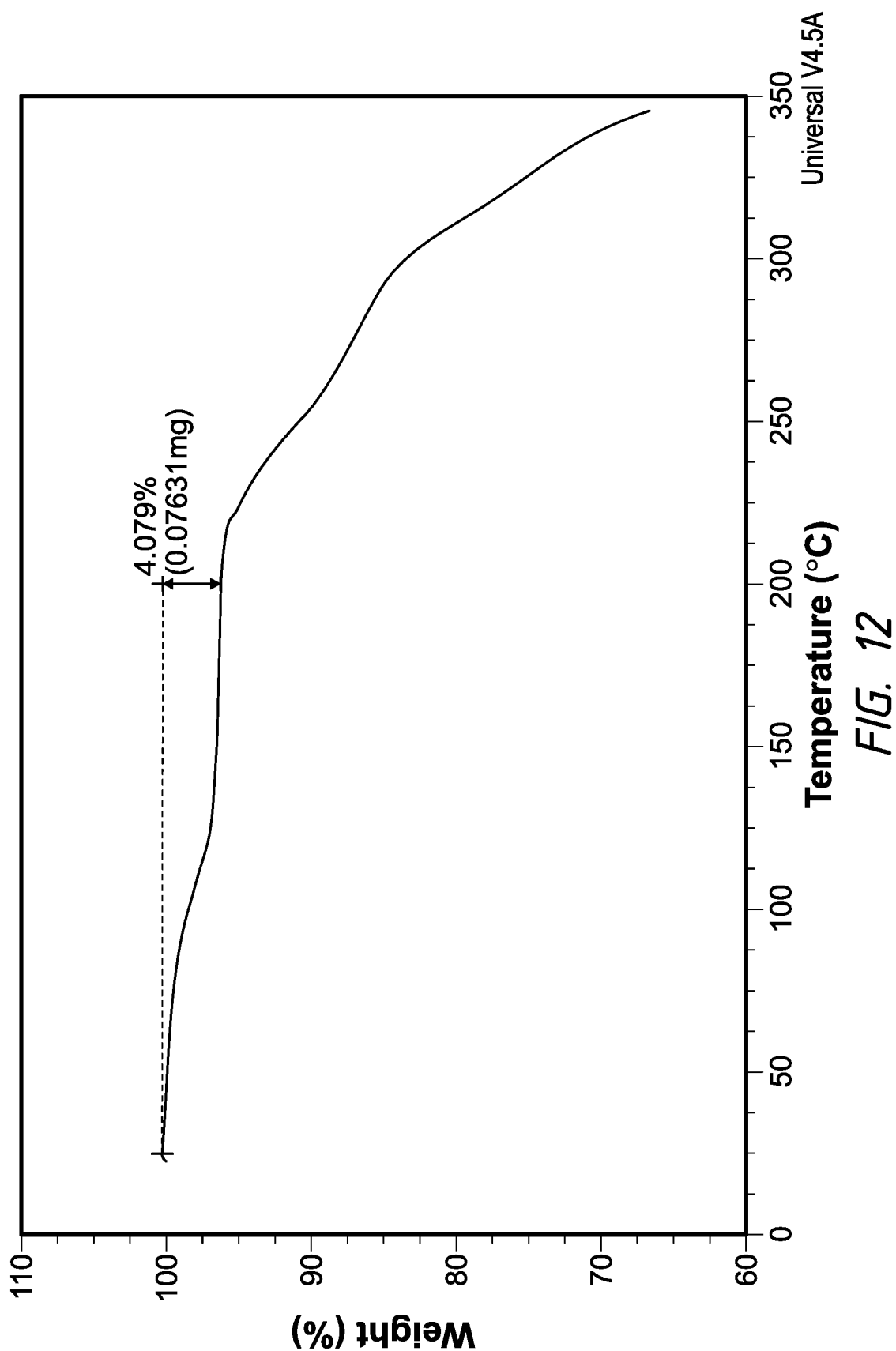
FIG. 12 is a representative TGA of Form D of fedratinib diHCl.

FIG. 12 is a representative TGA of Form D of fedratinib diHCl which shows a weight loss of about 4.1% up to about 200° C.

Figure 13:
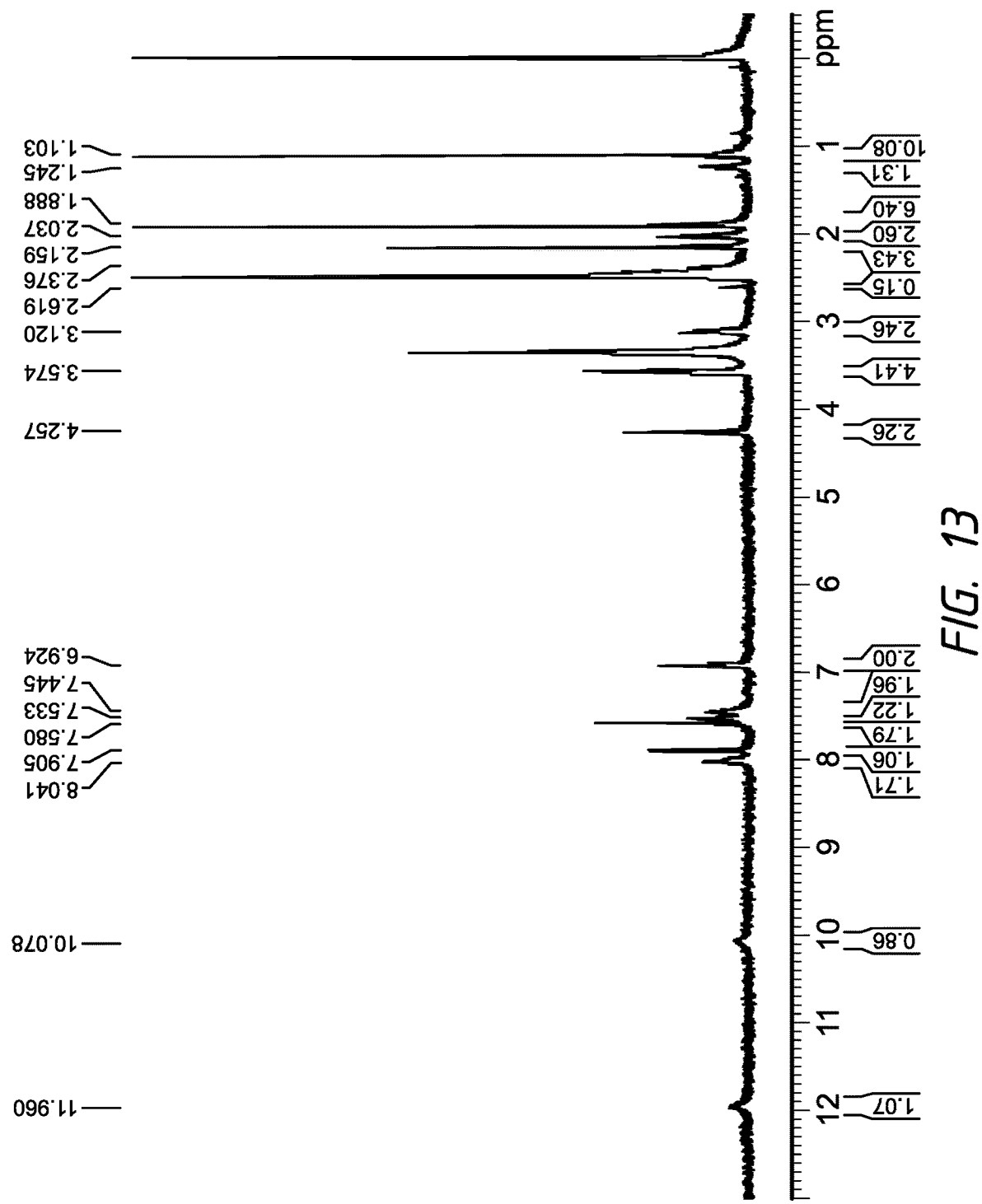
FIG. 13 is a $^1$H NMR spectra of Form D of fedratinib diHCl.

FIG. 13 is ¹H NMR spectra of Form D of fedratinib diHCl which includes a peak at about 11.960 ppm which is representative of a single proton of acetic acid.

Example 11—Preparation of Form E of Fedratinib diHCl 30.4 mg (0.05 mole) of Form A of fedratinib diHCl is dispersed in 0.2 mL of DMAc and slurried for 3 days at 20° C. The resulting material is analyzed by XRPD and determined to be Form E of fedratinib diHCl.

Form E of fedratinib diHCl is characterized by its XRPD pattern peaks. 2Θ and relative % intensity values for peaks are shown in Table 5.

TABLE 5

Average Peak List for Form E of fedratinib diHCl

| Angle 2-Theta ° | Intensity % |
|---|---|
| 11.8 | 32.1 |
| 12.2 | 8.5 |
| 12.6 | 100 |
| 13.6 | 18.8 |
| 14.0 | 27.6 |
| 14.6 | 31.4 |
| 15.1 | 74.1 |
| 16.0 | 41.6 |
| 16.4 | 7.2 |
| 17.0 | 73 |

TABLE 5-continued

Average Peak List for Form E of fedratinib diHCl

| Angle 2-Theta ° | Intensity % |
|---|---|
| 17.2 | 27 |
| 18.9 | 90.8 |
| 19.9 | 12.3 |
| 20.5 | 9.9 |
| 21.3 | 13.7 |
| 22.1 | 9.9 |
| 22.7 | 15.4 |
| 22.8 | 18.8 |
| 23.3 | 22.2 |
| 24.0 | 19.8 |
| 24.3 | 32.8 |
| 24.7 | 24.6 |
| 25.6 | 25.3 |
| 26.2 | 27.6 |
| 26.5 | 7.5 |
| 27.1 | 9.2 |
| 29.6 | 8.5 |
| 30.3 | 10.9 |
| 30.5 | 7.8 |
| 31.3 | 9.2 |
| 36.5 | 8.9 |

The angle measurements are ±0.2° 2Θ. In one embodiment, key defining peaks for solid-state Form E of fedratinib diHCl include two or more of 12.6, 15.1, and 18.9° 2Θ.

Figure 14:
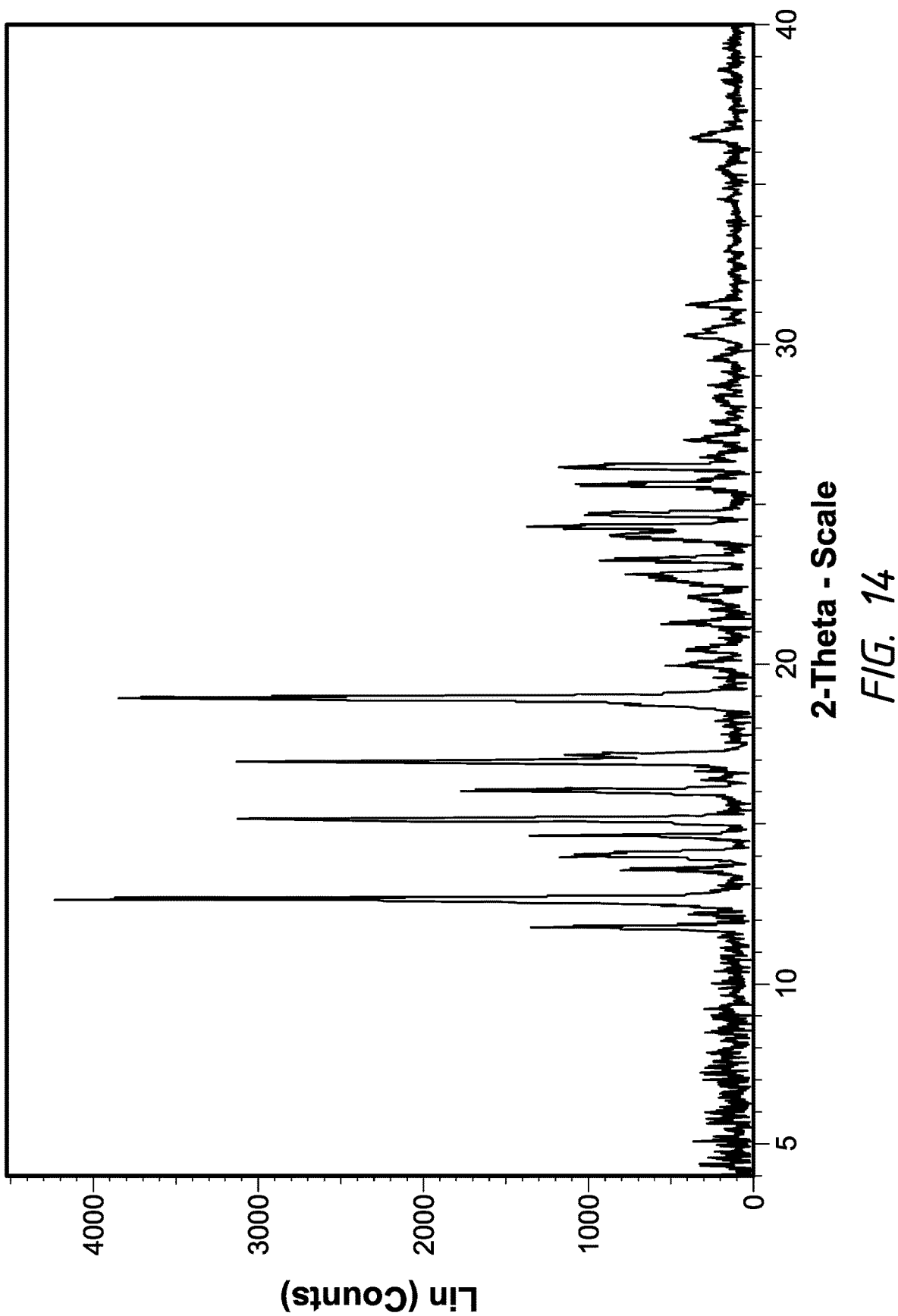
FIG. 14 is a representative XRPD pattern of Form E of fedratinib diHCl.

FIG. 14 is a representative XRPD pattern of Form E of fedratinib diHCl.

Figure 15:
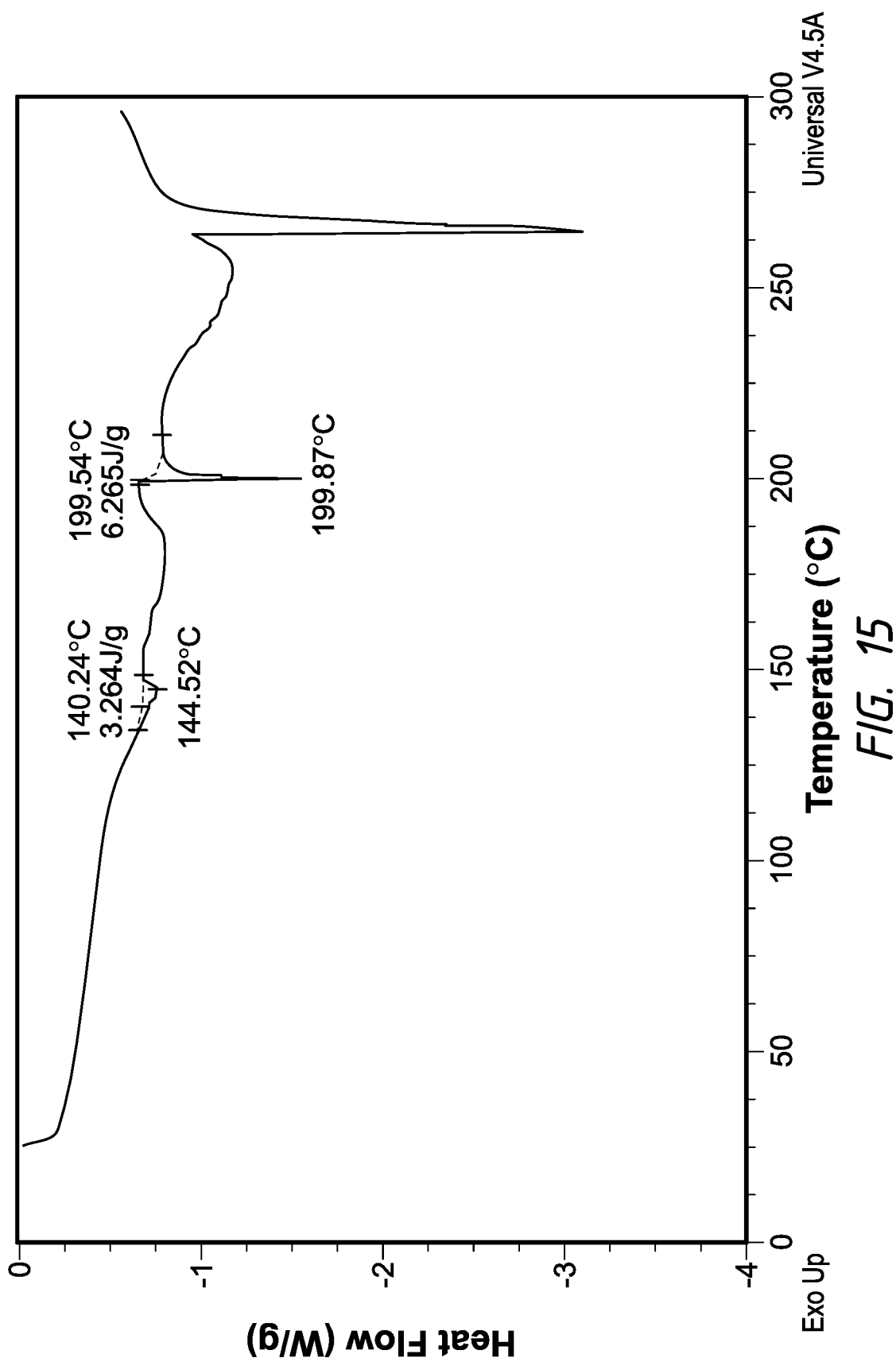
FIG. 15 is a representative DSC of Form E of fedratinib diHCl.

FIG. 15 is a representative DSC of Form E of fedratinib diHCl which shows endotherms with onset temperatures of about 140 and 200° C.

Figure 16:
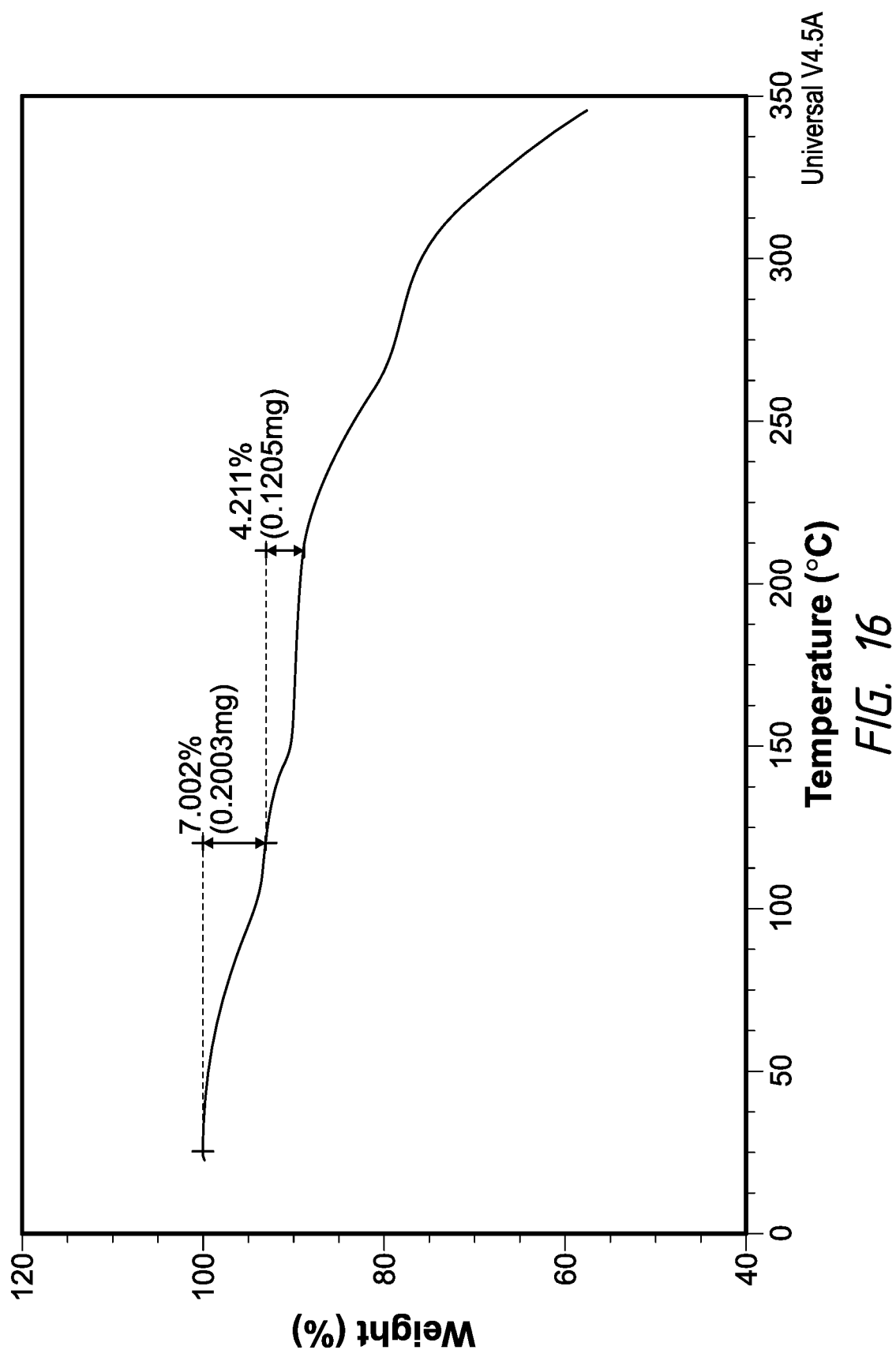
FIG. 16 is a representative TGA of Form E of fedratinib diHCl.

FIG. 16 is a representative TGA of Form E of fedratinib diHCl which shows a weight loss of about 7.0% followed by a secondary weight loss of about 4.2%.

Figure 17:
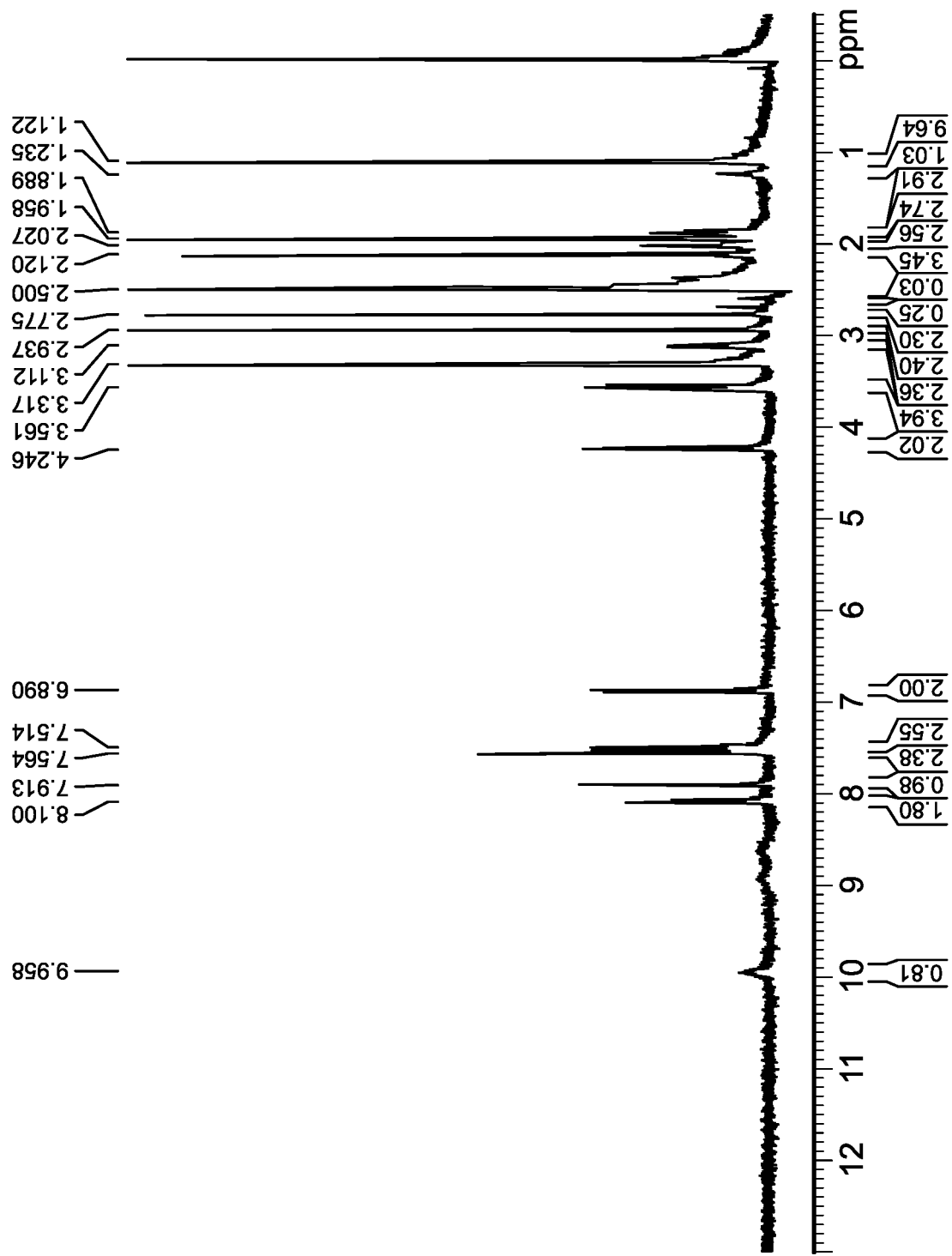
FIG. 17 is a $^1$H NMR spectra of Form E of fedratinib diHCl.

FIG. 17 is a $^1$H NMR spectra of Form E of fedratinib diHCl which includes a peak at about 1.958 ppm which is representative of three protons in DMAc.

Example 12—Preparation of Form F of Fedratinib diHCl 32.3 mg (0.05 mole) of Form A of fedratinib diHCl is dispersed in 0.2 mL of MeCN and slurried for 3 days at 20° C. The resulting material is analyzed by XRPD and determined to be Form F of fedratinib diHCl.

Form F of fedratinib diHCl is characterized by its XRPD pattern peaks. 2Θ and relative % intensity values for peaks are shown in Table 6.

TABLE 6

Average Peak List for Form F of fedratinib diHCl

| Angle 2-Theta ° | Intensity % |
|---|---|
| 9.4 | 10.4 |
| 9.7 | 10.1 |
| 10.9 | 10.4 |
| 12.0 | 100 |
| 12.3 | 33 |
| 12.5 | 8.8 |
| 13.0 | 15.2 |
| 13.3 | 12.8 |
| 13.6 | 29.3 |
| 14.0 | 12.5 |
| 14.3 | 12.1 |
| 14.8 | 13.8 |
| 15.0 | 10.1 |
| 15.8 | 19.9 |
| 16.1 | 11.1 |
| 16.5 | 29.6 |
| 16.7 | 31.3 |
| 17.3 | 13.8 |
| 17.6 | 15.8 |
| 17.8 | 38.4 |
| 19.5 | 14.1 |
| 19.8 | 25.3 |
| 20.7 | 10.8 |
| 21.2 | 17.5 |
| 21.5 | 56.2 |
| 23.4 | 16.5 |
| 23.8 | 75.1 |
| 24.4 | 33.7 |
| 24.7 | 8.8 |
| 25.1 | 12.8 |
| 25.5 | 46.1 |
| 25.9 | 7.4 |
| 26.7 | 10.1 |
| 27.0 | 10.8 |
| 27.6 | 19.2 |
| 28.9 | 6.1 |
| 29.7 | 7.4 |
| 30.2 | 6.4 |
| 30.8 | 4.7 |
| 31.1 | 5.1 |
| 31.7 | 6.4 |
| 33.6 | 5.4 |
| 34.1 | 5.7 |

The angle measurements are ±0.2° 2Θ. In one embodiment, key defining peaks for solid-state Form F of fedratinib diHCl include two or more of 12.0, 21.5, and 23.8° 2Θ.

Figure 18:
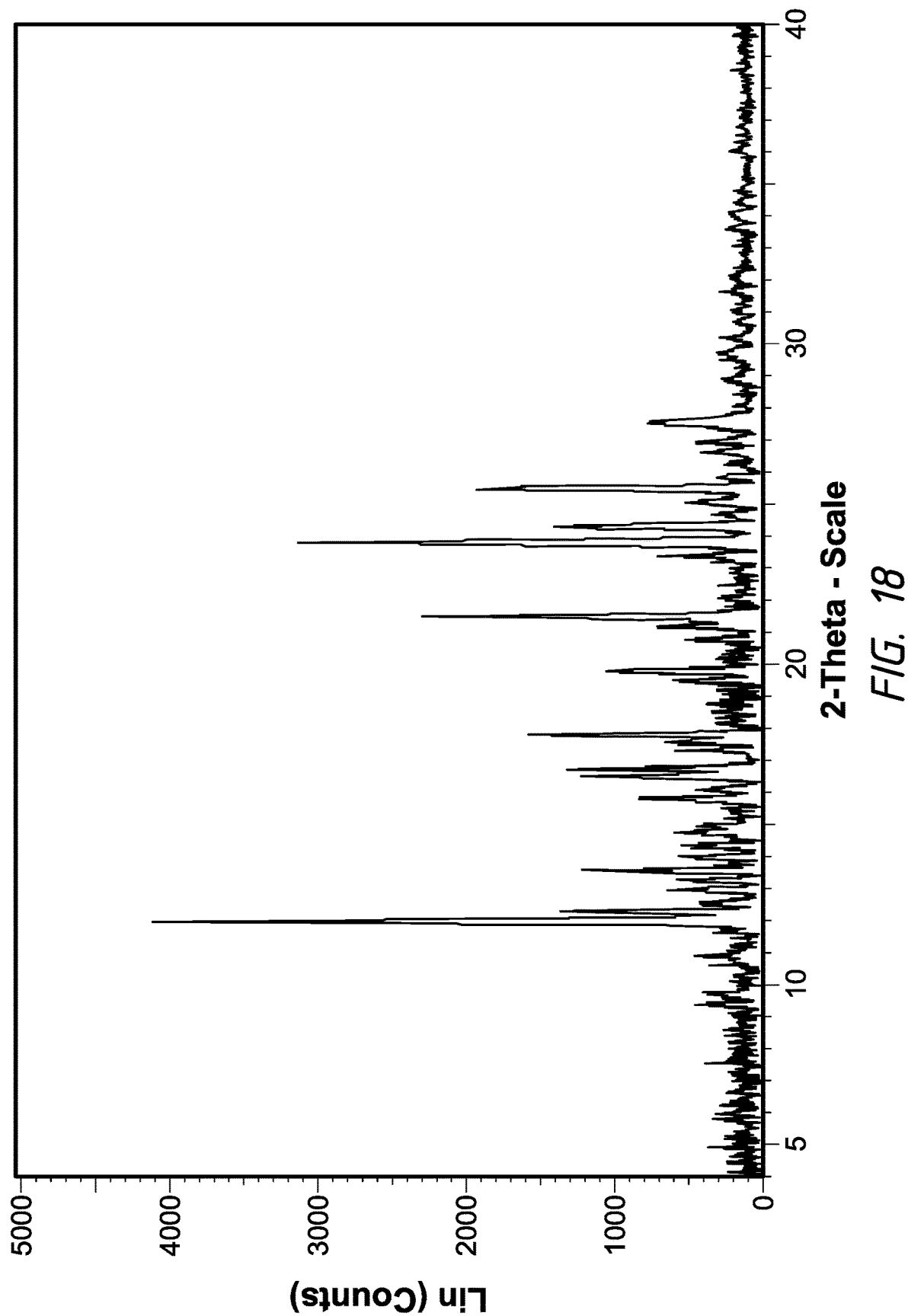
FIG. 18 is a representative XRPD pattern of Form F of fedratinib diHCl.

FIG. 18 is a representative XRPD pattern of Form F of fedratinib diHCl.

Figure 19:
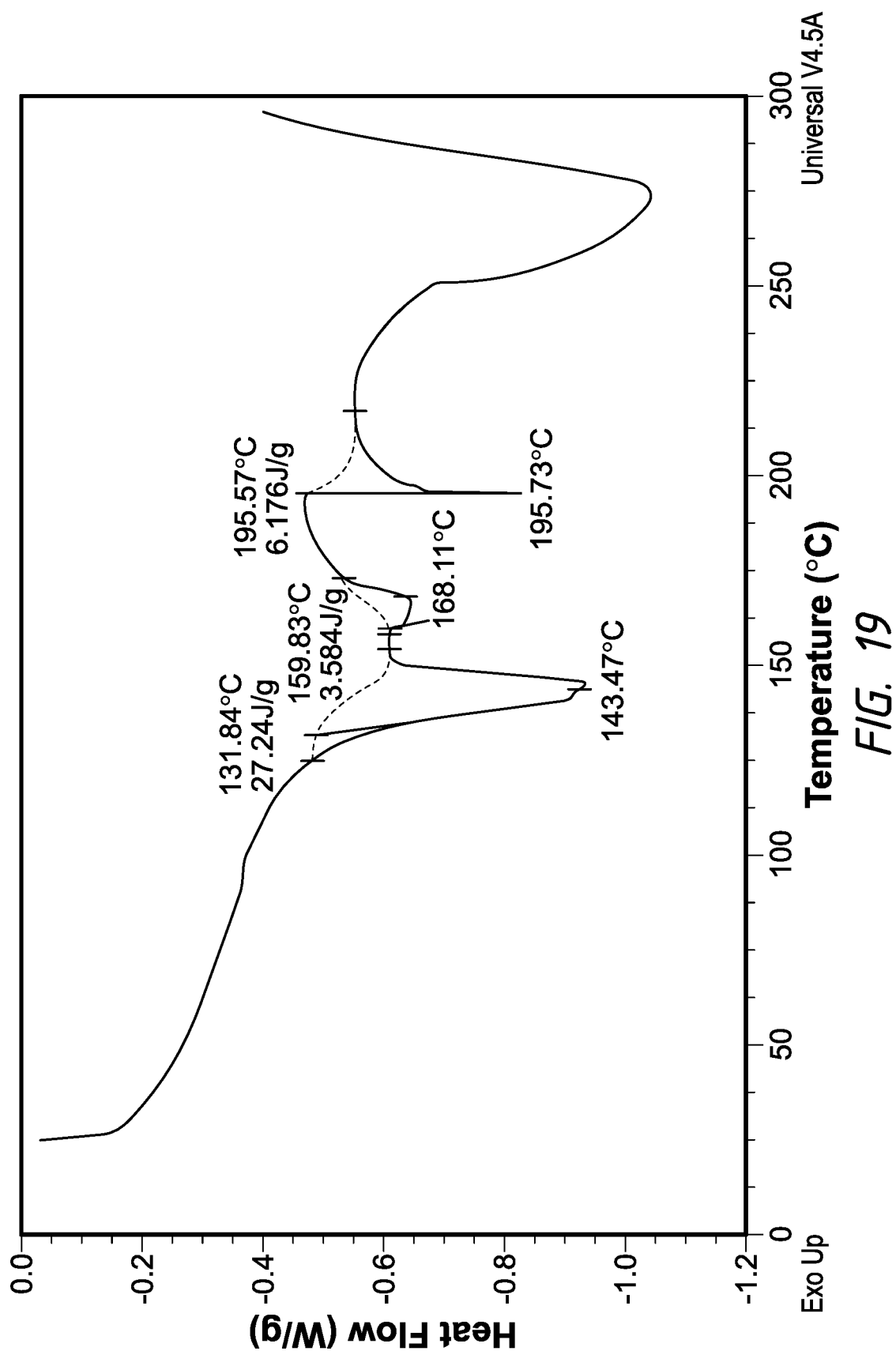
FIG. 19 is a representative DSC of Form F of fedratinib diHCl.

FIG. 19 is a representative DSC of Form F of fedratinib diHCl which shows multiple endotherms with onset temperatures at about 132, 160 and 196° C.

Figure 20:
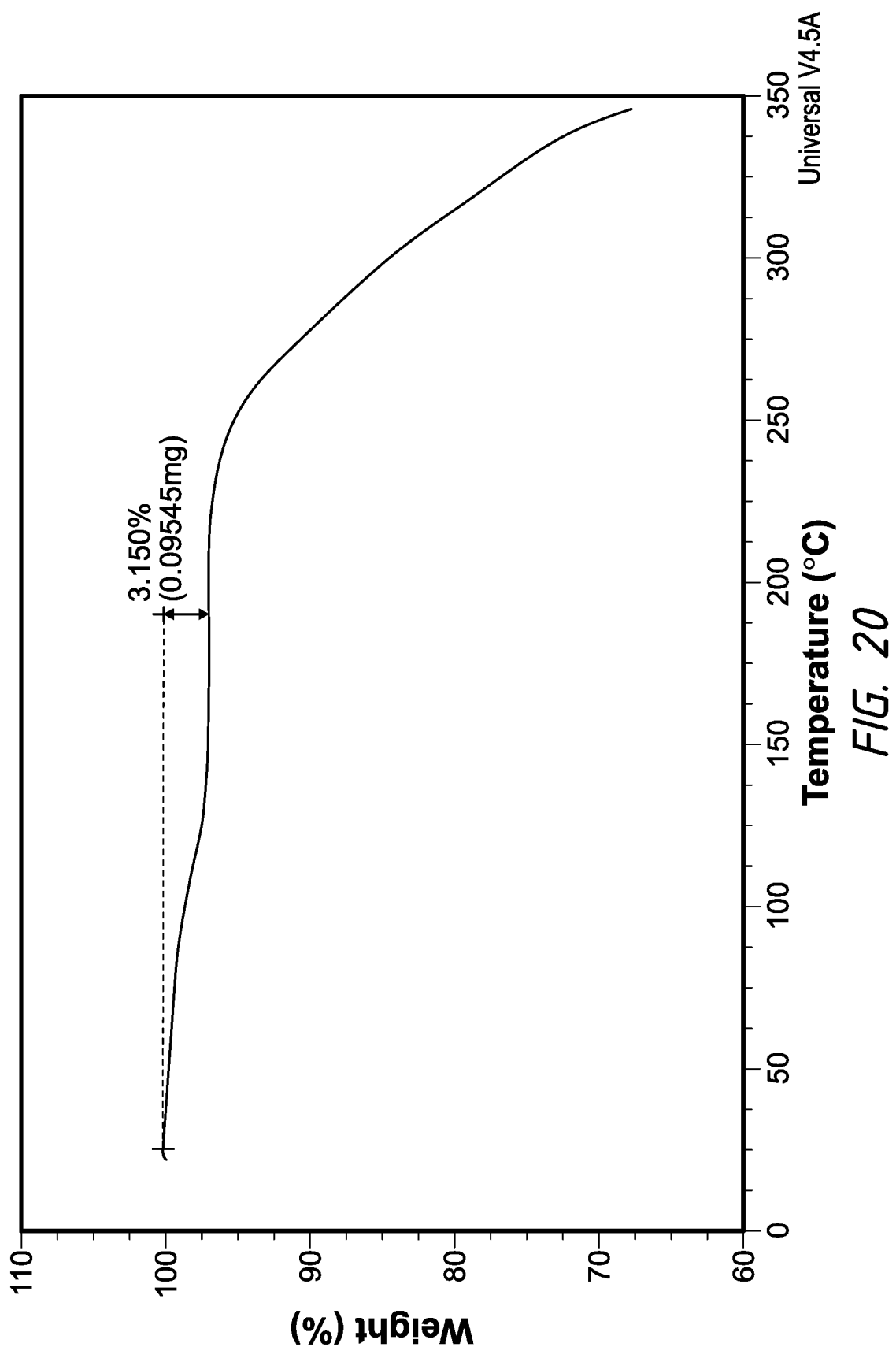
FIG. 20 is a representative TGA of Form F of fedratinib diHCl.

FIG. 20 is a representative TGA of Form F of fedratinib diHCl which shows a weight loss of about 3.2% up to about 190° C.

Figure 21:
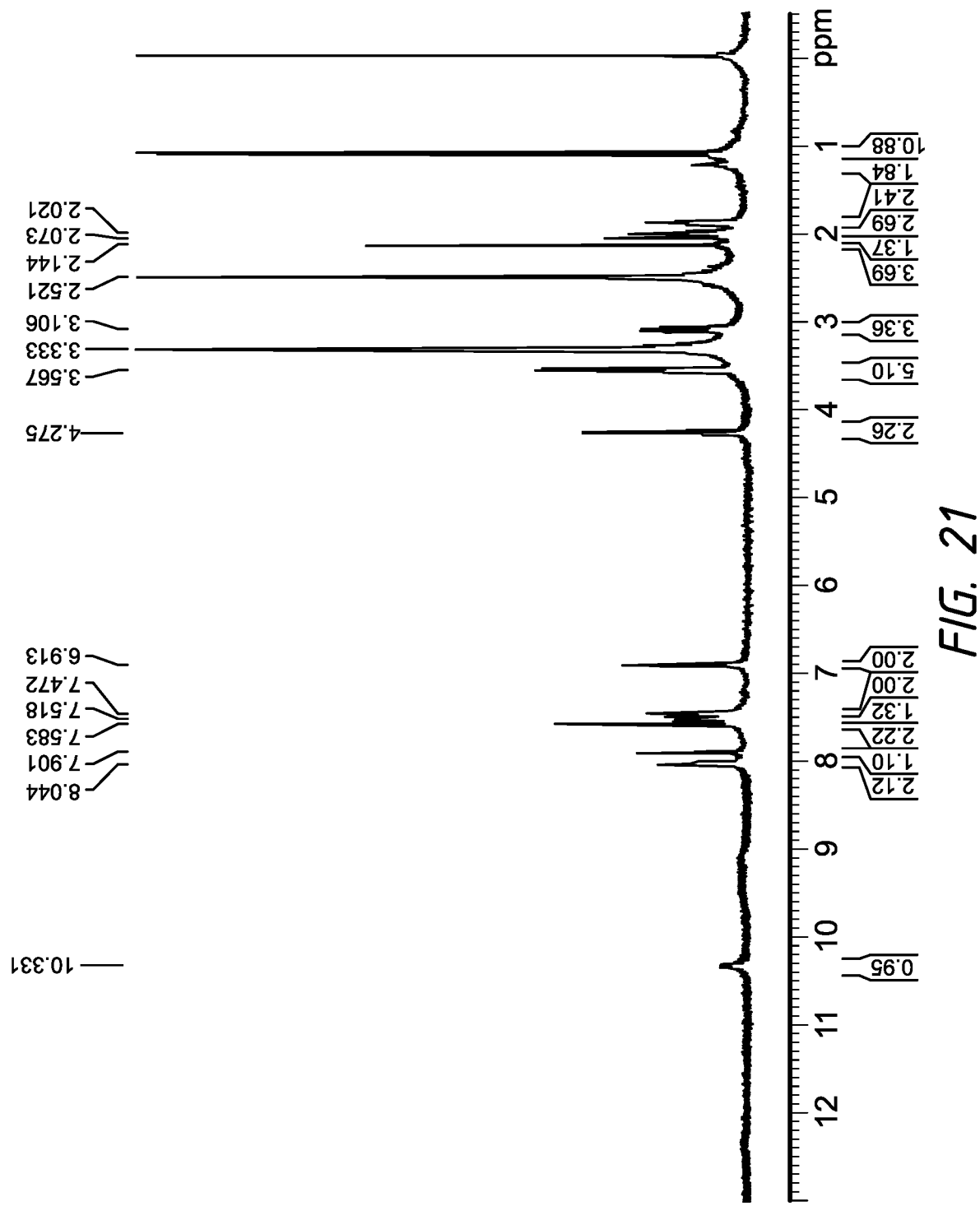
FIG. 21 is a $^1$H NMR spectra of Form F of fedratinib diHCl.

FIG. 21 is a $^1$H NMR spectra of Form F of fedratinib diHCl which includes a peak at about 2.073 ppm which is representative of three protons in MeCN.

Example 13—Preparation of Amorphous Fedratinib diHCl

Form A of fedratinib diHCl is heated to about 190° C. by DSC at the heating rate of 10° C./min. The sample is collected and analyzed by XRPD and determined to be amorphous fedratinib diHCl.

Figure 22:
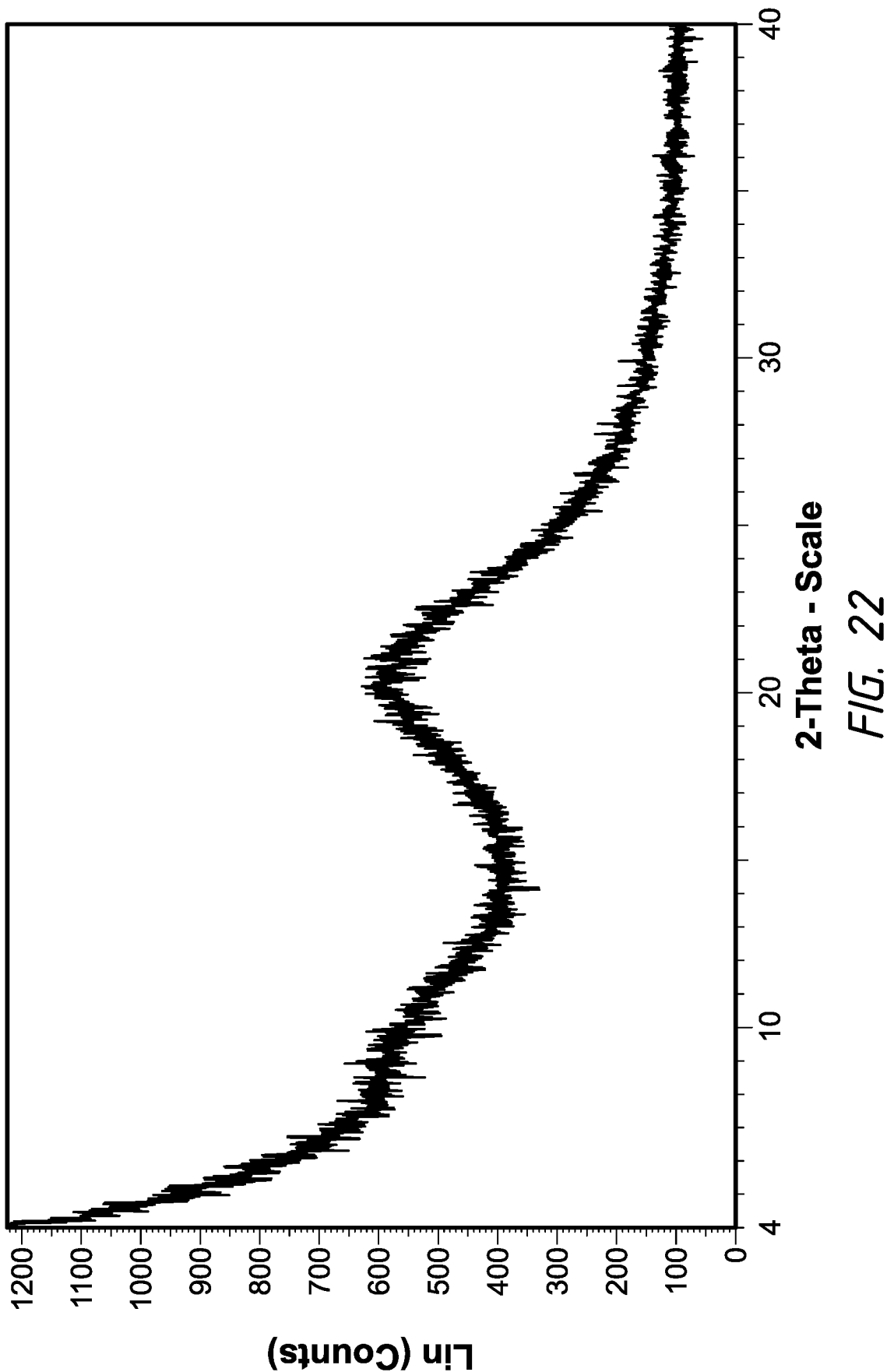
FIG. 22 is a representative XRPD pattern of amorphous fedratinib diHCl.

FIG. 22 is a representative XRPD pattern of amorphous fedratinib diHCl.

Figure 23:
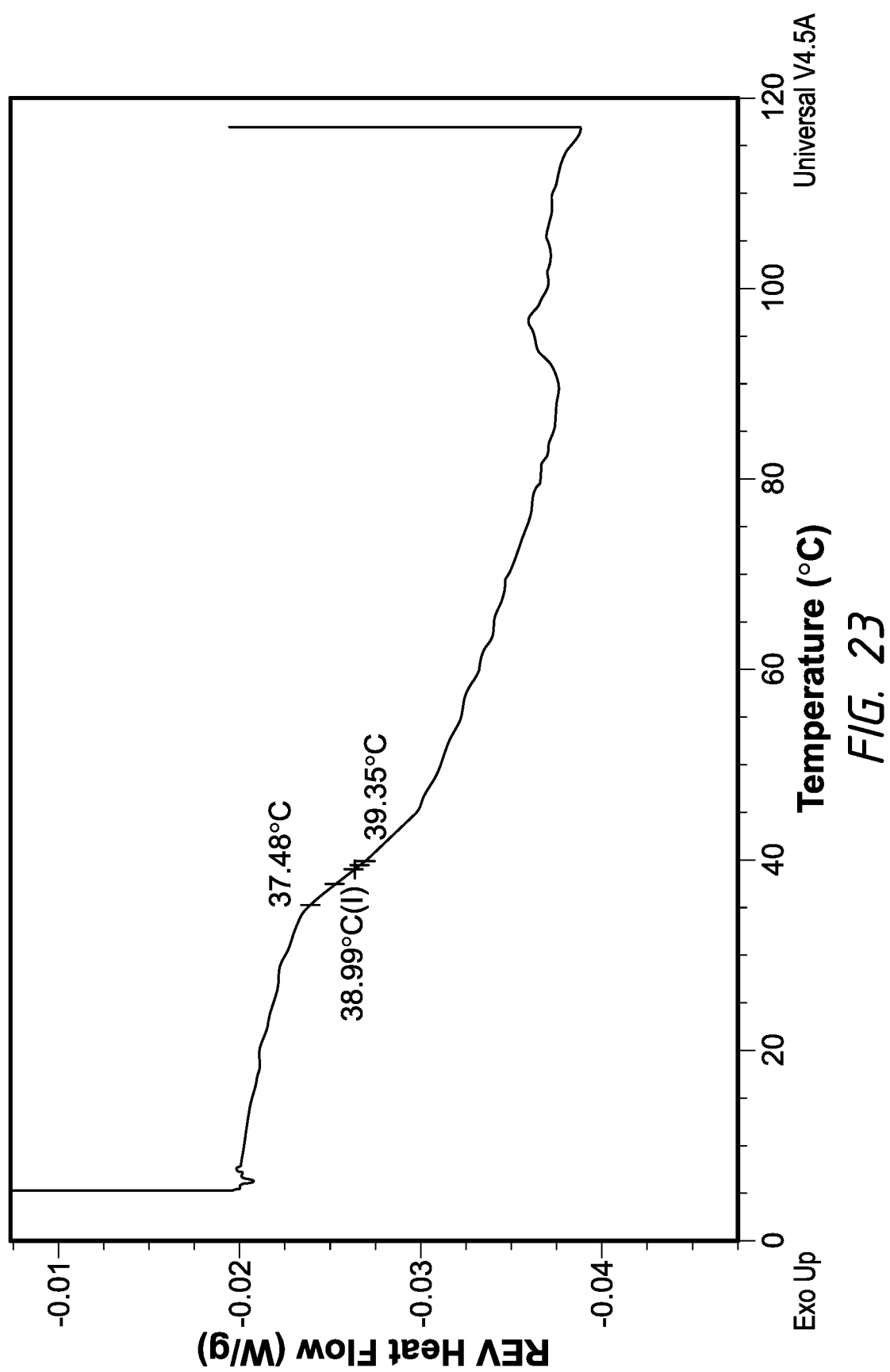
FIG. 23 is a representative mDSC of amorphous fedratinib diHCl.

FIG. 23 is a representative mDSC of amorphous fedratinib diHCl which shows a glass transition temperature (Tg) of 39° C.±2° C.

Example 14—Preparation of Amorphous Fedratinib diHCl

Form F of fedratinib diHCl is heated to about 150° C. by DSC at the heating rate of 10° C./min. The sample is collected and analyzed by XRPD and determined to be amorphous fedratinib diHCl.

Example 15—Preparation of Amorphous Fedratinib diHCl

Form E of fedratinib diHCl is heated to about 160° C. by DSC at the heating rate of 10° C./min. The sample is collected and analyzed by XRPD and determined to be amorphous fedratinib diHCl.

Example 16—Preparation of Amorphous Fedratinib diHCl

Form A of fedratinib diHCl is subjected to DVS with initial exposure to 50% relative humidity. The relative humidity is then increased to 90% with a 10% increase in humidity at each step. The relative humidity is then decreased to 0% with a 10% decrease in humidity at each step. This cycle is repeated 3 times. The sample is collected and analyzed by XRPD and determined to be amorphous fedratinib diHCl.

Example 17—Preparation of Fedratinib diHCl Co-Crystal with Succinic Acid 30 mg (0.05 mole) of Form A of fedratinib diHCl is suspended in 0.15 mL of MeOH:acetone (1:2, v/v) at 20° C. 5.9 mg (0.05 mole) of succinic acid is suspended in 0.03 mL of MeOH:acetone (1:2, v/v). The fedratinib diHCl suspension is mixed with the succinic acid suspension and the mixture is stirred at 20° C. for 6 hours followed by cooling to 4° C. at the cooling rate of 0.1° C./min. The resulting material is analyzed and determined to be a fedratinib diHCl co-crystal with succinic acid.

Fedratinib diHCl co-crystal with succinic acid is characterized by its XRPD pattern peaks. 2Θ and relative % intensity values for peaks are shown in Table 7.

TABLE 7

Average Peak List for fedratinib diHCl co-crystal with succinic acid

| Angle 2-Theta ° | Intensity % % |
|---|---|
| 4.5 | 94.2 |
| 5.6 | 32.9 |
| 8.1 | 29.7 |
| 9.2 | 100 |
| 9.8 | 45.2 |
| 11.1 | 45.8 |
| 11.5 | 26.5 |
| 13.8 | 15.5 |
| 14.0 | 17.4 |
| 14.4 | 14.2 |
| 15.6 | 67.1 |
| 17.2 | 17.4 |
| 17.7 | 34.2 |
| 18.2 | 15.5 |
| 18.8 | 34.8 |
| 19.3 | 21.3 |
| 19.5 | 24.5 |
| 22.4 | 20 |
| 24.3 | 16.8 |
| 28.0 | 16.1 |

The angle measurements are ±0.2° 2Θ. In one embodiment, key defining peaks for solid-state fedratinib diHCl co-crystal with succinic acid include two or more of 4.5, 9.2, and 15.6° 2Θ.

Figure 24:
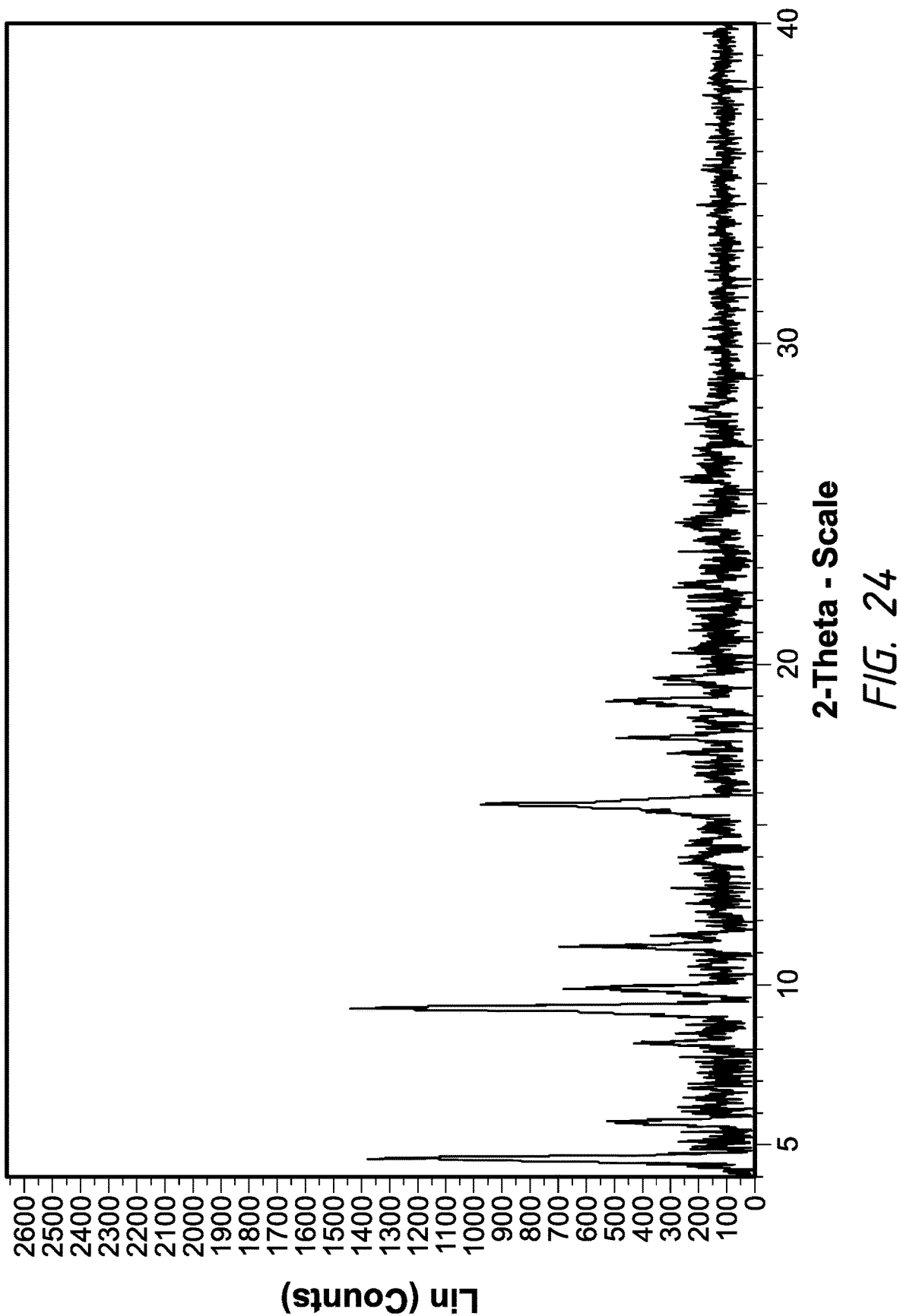
FIG. 24 is a representative XRPD pattern of fedratinib diHCl co-crystal with succinic acid.

FIG. 24 is a representative XRPD pattern of fedratinib diHCl co-crystal with succinic acid.

Figure 25:
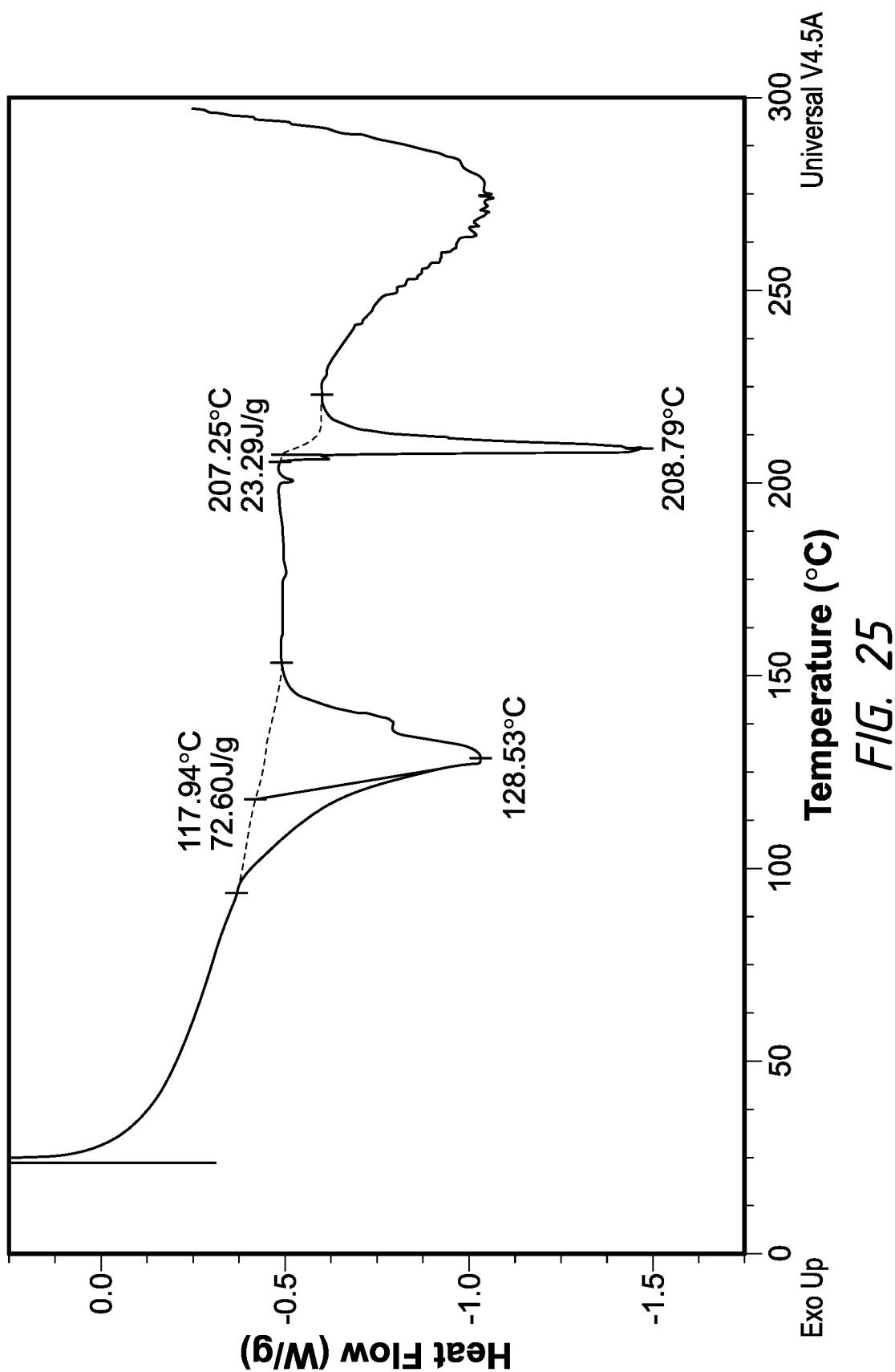
FIG. 25 is a representative DSC of fedratinib diHCl co-crystal with succinic acid.

FIG. 25 is a representative DSC of fedratinib diHCl co-crystal with succinic acid which shows endotherms with onset temperatures at about 118 and 207° C.

Figure 26:
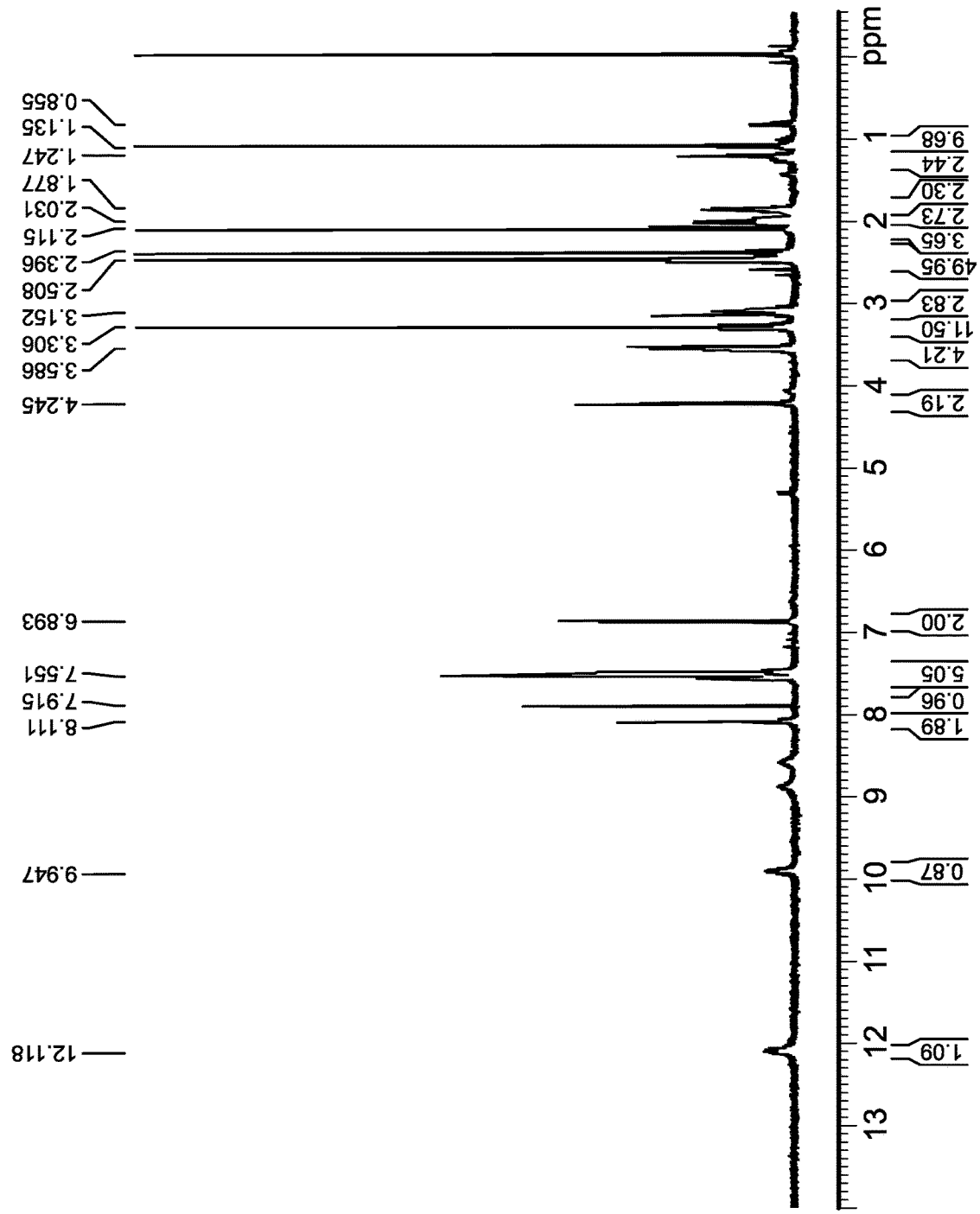
FIG. 26 is a $^1$H NMR spectra of fedratinib diHCl co-crystal with succinic acid.

FIG. 26 is a $^1$H NMR spectra of fedratinib diHCl co-crystal with succinic acid which indicates a 2:1 (fedratinib diHCl:succinic acid) cocrystal, with a peak at about 12.118 ppm from two protons of succinic acid, and a peak at about 6.893 ppm from two protons of fedratinib diHCl.

Example 18—Preparation of Fedratinib diHCl Co-Crystal with Fumaric Acid 30 mg (0.05 mole) of Form A of fedratinib diHCl is suspended in 0.15 mL of MeOH:acetone (1:2, v/v) at 20° C. 5.8 mg (0.05 mole) of fumaric acid is suspended in 0.03 mL of MeOH:acetone (1:2, v/v). The fedratinib diHCl suspension is mixed with the fumaric acid suspension and the mixture is stirred at 20° C. for 6 hours followed by cooling to 4° C. at the cooling rate of 0.1° C./min. The resulting material is analyzed and determined to be a fedratinib diHCl co-crystal with fumaric acid.

Fedratinib diHCl co-crystal with fumaric acid is characterized by its XRPD pattern peaks. 2Θ and relative % intensity values for peaks are shown in Table 8.

TABLE 8

Average Peak List for fedratinib diHCl co-crystal with fumaric acid

| Angle 2-Theta ° | Intensity % % |
|---|---|
| 4.6 | 40.1 |
| 5.7 | 30.7 |
| 6.1 | 21.9 |
| 8.2 | 26.6 |
| 9.1 | 33 |
| 9.4 | 100 |
| 9.7 | 23.7 |
| 10.0 | 41.5 |
| 11.2 | 45.6 |
| 11.6 | 29.5 |
| 13.8 | 21.1 |
| 14.2 | 24.3 |
| 15.5 | 29.2 |
| 15.8 | 55.3 |
| 16.2 | 14.6 |
| 17.3 | 16.7 |
| 17.8 | 38 |
| 18.0 | 12.3 |
| 18.6 | 15.8 |
| 19.0 | 26.6 |
| 19.6 | 19.6 |
| 20.1 | 16.4 |
| 20.7 | 16.1 |
| 22.5 | 14 |

The angle measurements are ±0.2° 2Θ. In one embodiment, key defining peaks for solid-state fedratinib diHCl co-crystal with fumaric acid include two or more of 9.4, 11.2, and 15.8° 2Θ.

Figure 27:
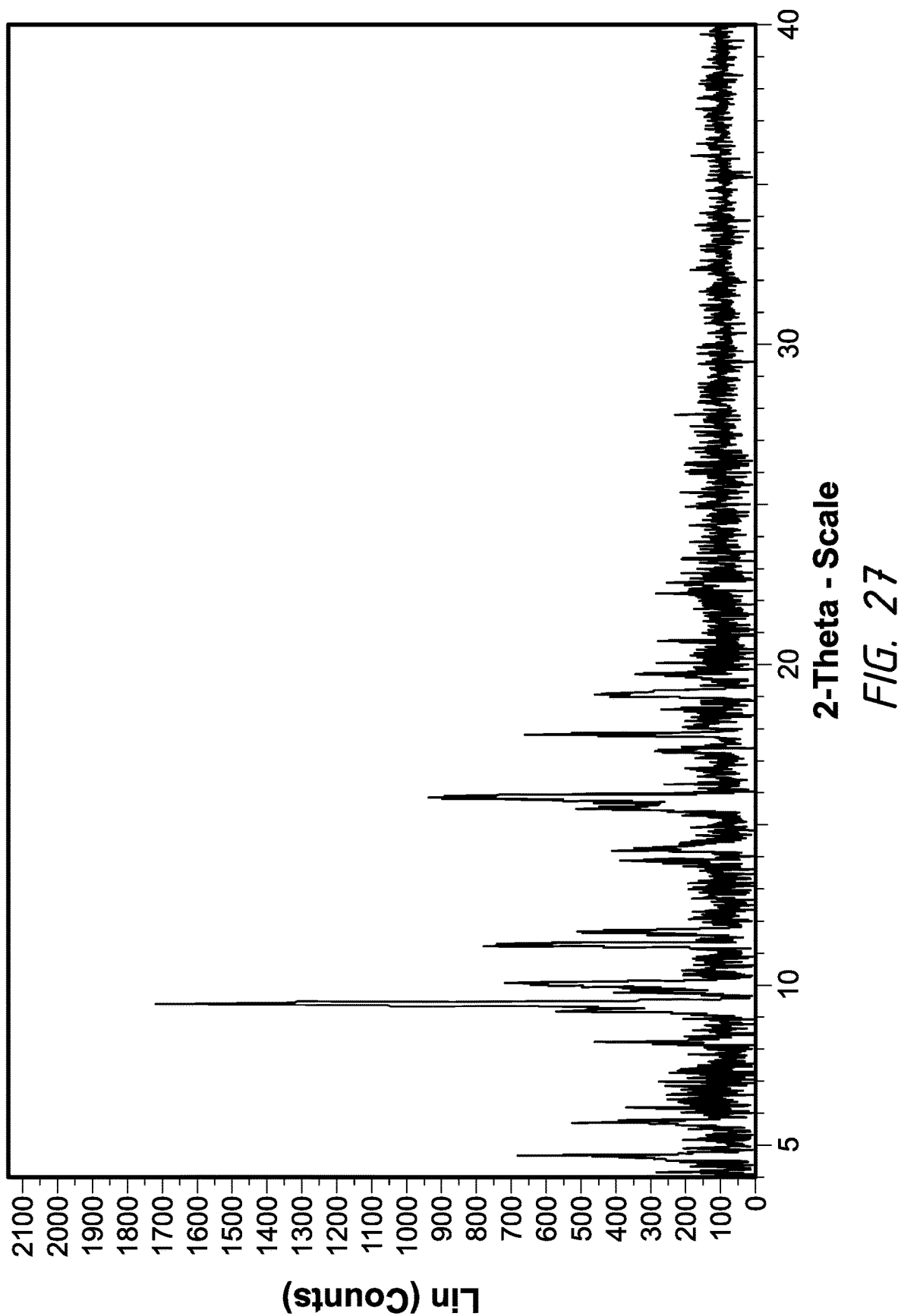
FIG. 27 is a representative XRPD pattern of fedratinib diHCl co-crystal with fumaric acid.

FIG. 27 is a representative XRPD pattern of fedratinib diHCl co-crystal with fumaric acid.

Figure 28:
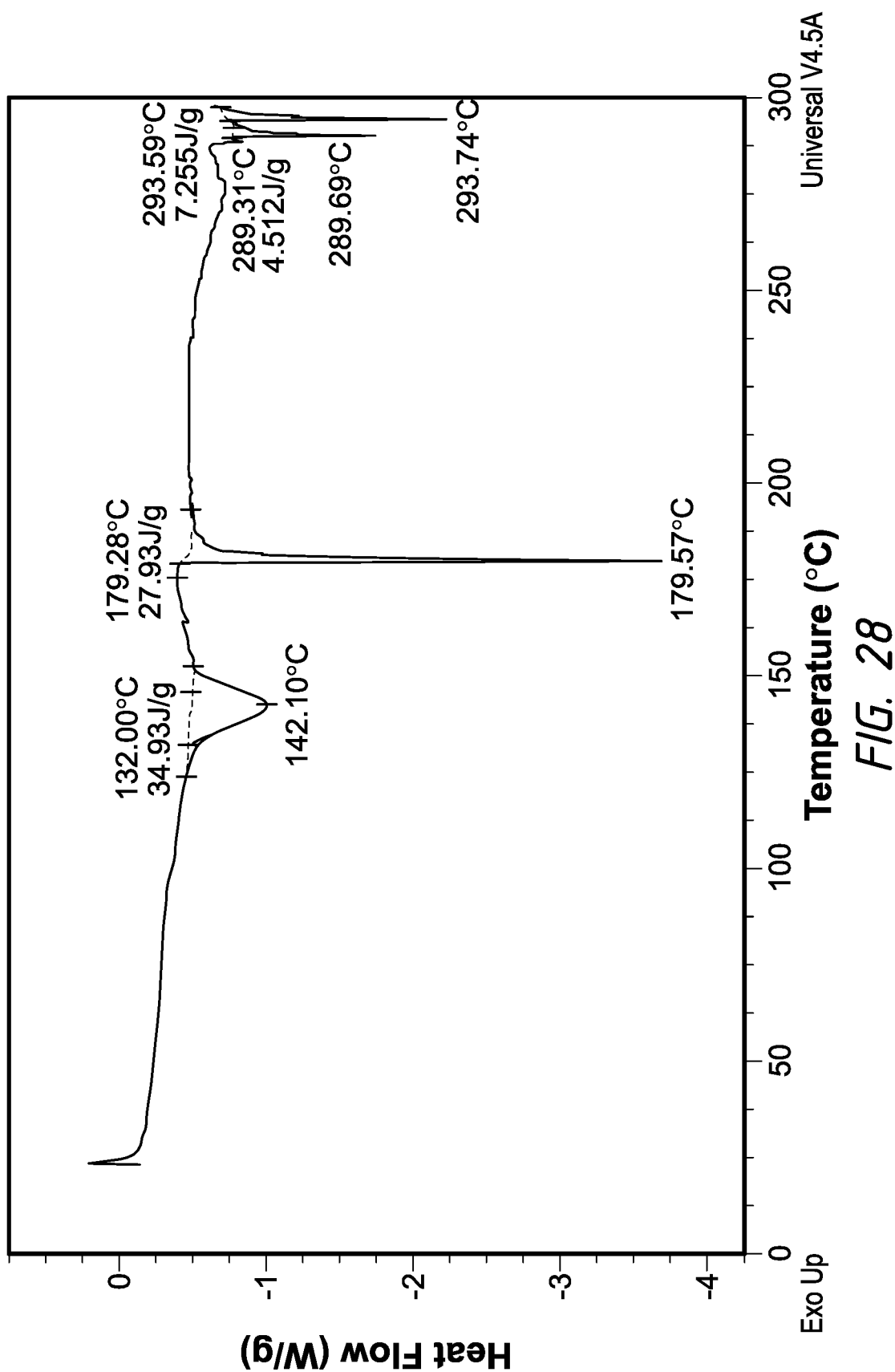
FIG. 28 is a representative DSC of fedratinib diHCl co-crystal with fumaric acid.

FIG. 28 is a representative DSC of fedratinib diHCl co-crystal with fumaric acid which shows multiple endotherms with onset temperatures at about 132, 179, 289 and 294° C. The endotherms at 289 and 294° C. are likely due to the presence of extra fumaric acid in the fedratinib diHCl fumaric acid co-crystal.

Figure 29:
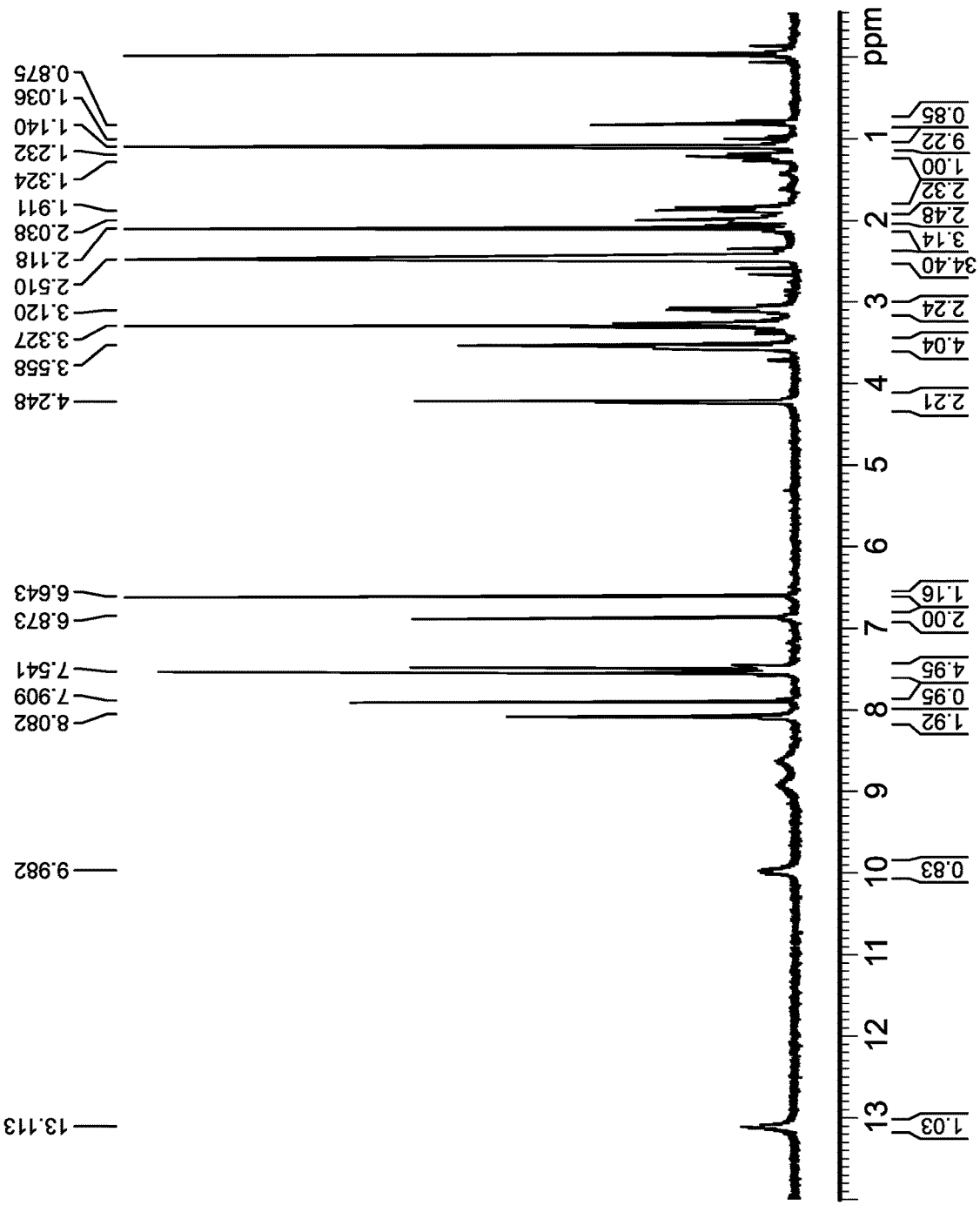
FIG. 29 is a $^1$H NMR spectra of fedratinib diHCl co-crystal with fumaric acid.

FIG. 29 is a $^1$H NMR spectra of fedratinib diHCl co-crystal with fumaric acid which indicates a 2:1 (fedratinib diHCl:fumaric acid) cocrystal, with a peak at about 13.113 ppm from two protons of fumaric acid, and a peak at about 6.873 ppm from two protons of fedratinib diHCl.

A comparison of FIG. 24 and FIG. 27 suggests that fedratinib diHCl co-crystal with succinic acid and fedratinib diHCl co-crystal with fumaric acid have very similar XRPD patterns.

Example 19—Preparation of Fedratinib diHCl Co-Crystal with Sucrose 30 mg (0.05 mole) of Form A of fedratinib diHCl and 17.2 mg (0.05 mole) of sucrose are respectively suspended in 0.15 and 0.03 mL of MeOH:acetone (1:2, v/v) at 20° C. The two suspensions are then mixed and stirred at 20° C. for 6 hours followed by cooling to 4° C. at the cooling rate of 0.1° C./min. The resulting material is analyzed and determined to be a fedratinib diHCl co-crystal with sucrose.

Fedratinib diHCl co-crystal with sucrose is characterized by its XRPD pattern peaks. 2Θ and relative % intensity values for peaks are shown in Table 9.

TABLE 9

Average Peak List for fedratinib diHCl co-crystal with sucrose

| Angle 2-Theta ° | Intensity % % |
|---|---|
| 8.1 | 21.7 |
| 9.3 | 26.8 |
| 10.0 | 13.8 |
| 11.2 | 20.1 |
| 11.5 | 100 |
| 12.0 | 45.7 |
| 12.5 | 24.8 |
| 12.9 | 63.8 |
| 13.3 | 13 |
| 14.3 | 13 |
| 14.5 | 11.4 |
| 15.3 | 26.8 |
| 15.9 | 26.4 |
| 16.2 | 10.6 |
| 16.5 | 12.6 |
| 16.7 | 10.6 |
| 18.6 | 81.9 |
| 19.4 | 98 |
| 19.7 | 13.4 |
| 20.2 | 25.6 |
| 20.6 | 24 |
| 21.5 | 15 |
| 21.8 | 26 |
| 22.3 | 15 |
| 22.4 | 15.4 |
| 23.4 | 36.2 |
| 23.9 | 16.1 |
| 24.4 | 29.5 |
| 24.6 | 87.8 |
| 25.0 | 39.8 |
| 26.3 | 18.1 |
| 27.5 | 14.2 |
| 28.5 | 13 |
| 30.4 | 10.6 |
| 30.8 | 22.8 |
| 31.7 | 22.8 |
| 32.4 | 13.8 |
| 32.8 | 8.3 |
| 33.2 | 9.4 |
| 34.6 | 11 |
| 35.9 | 10.2 |
| 37.1 | 11.8 |
| 38.1 | 17.7 |
| 38.3 | 16.5 |
| 39.7 | 11 |

The angle measurements are ±0.2° 2Θ. In one embodiment, key defining peaks for solid-state fedratinib diHCl co-crystal with sucrose include two or more of 11.5, 19.4, and 24.6° 2Θ.

Figure 30:
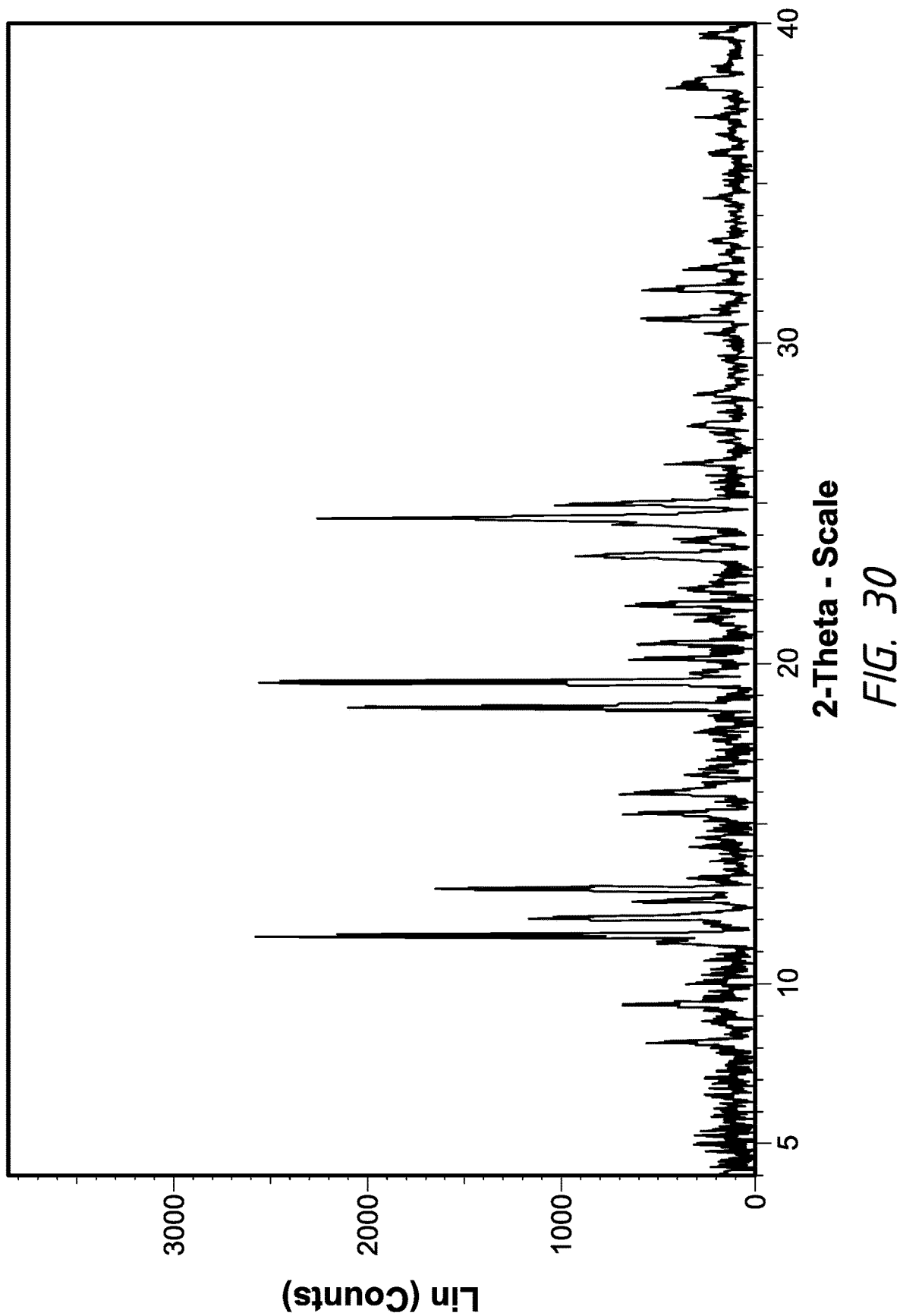
FIG. 30 is a representative XRPD pattern of fedratinib diHCl co-crystal with sucrose.

FIG. 30 is a representative XRPD pattern of fedratinib diHCl co-crystal with sucrose.

Figure 31:
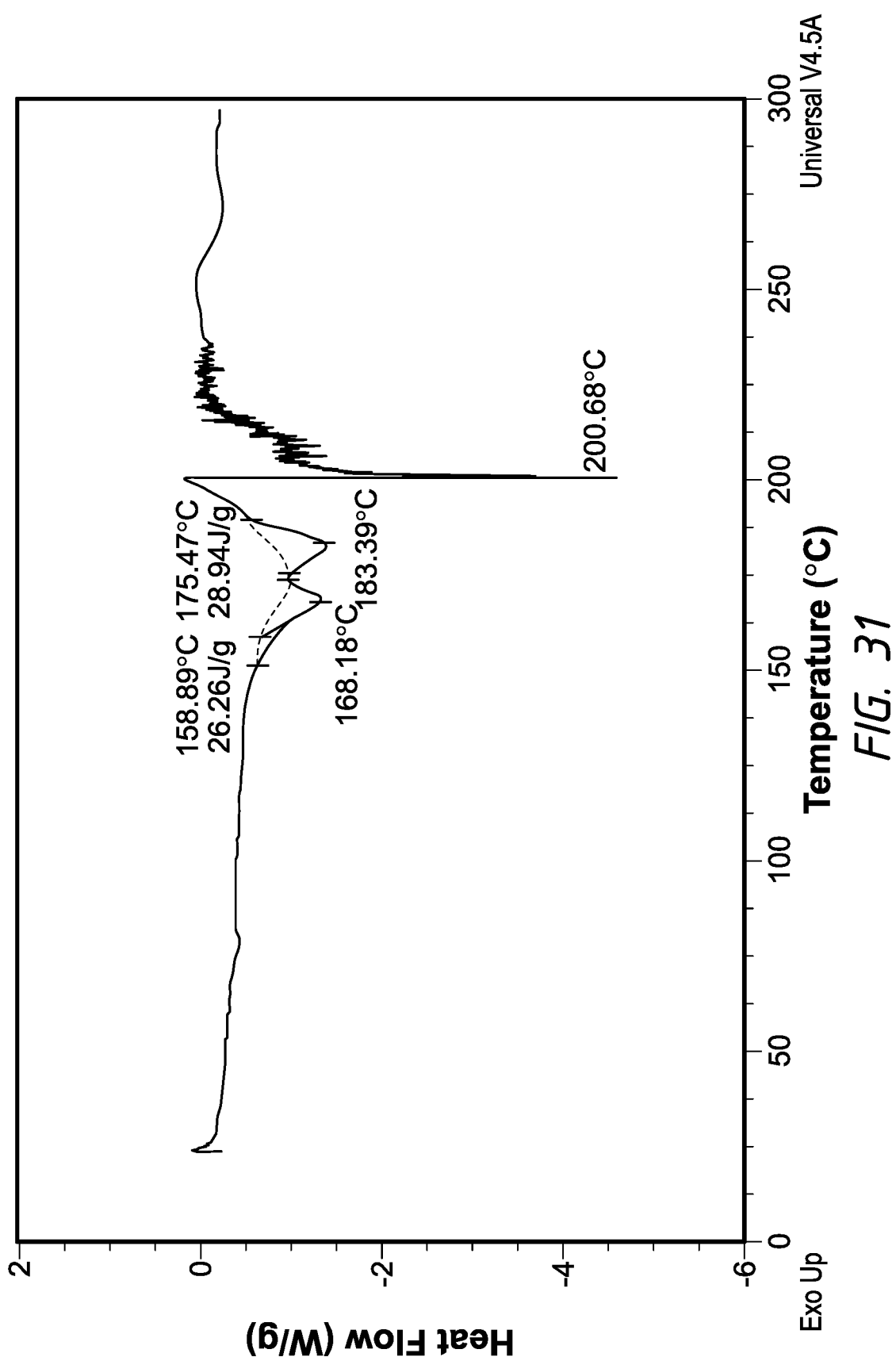
FIG. 31 is a representative DSC of fedratinib diHCl co-crystal with sucrose.

FIG. 31 is a representative DSC of fedratinib diHCl co-crystal with sucrose which shows multiple endotherms with onset temperatures at about 159, 175 and 201° C.

Figure 32:
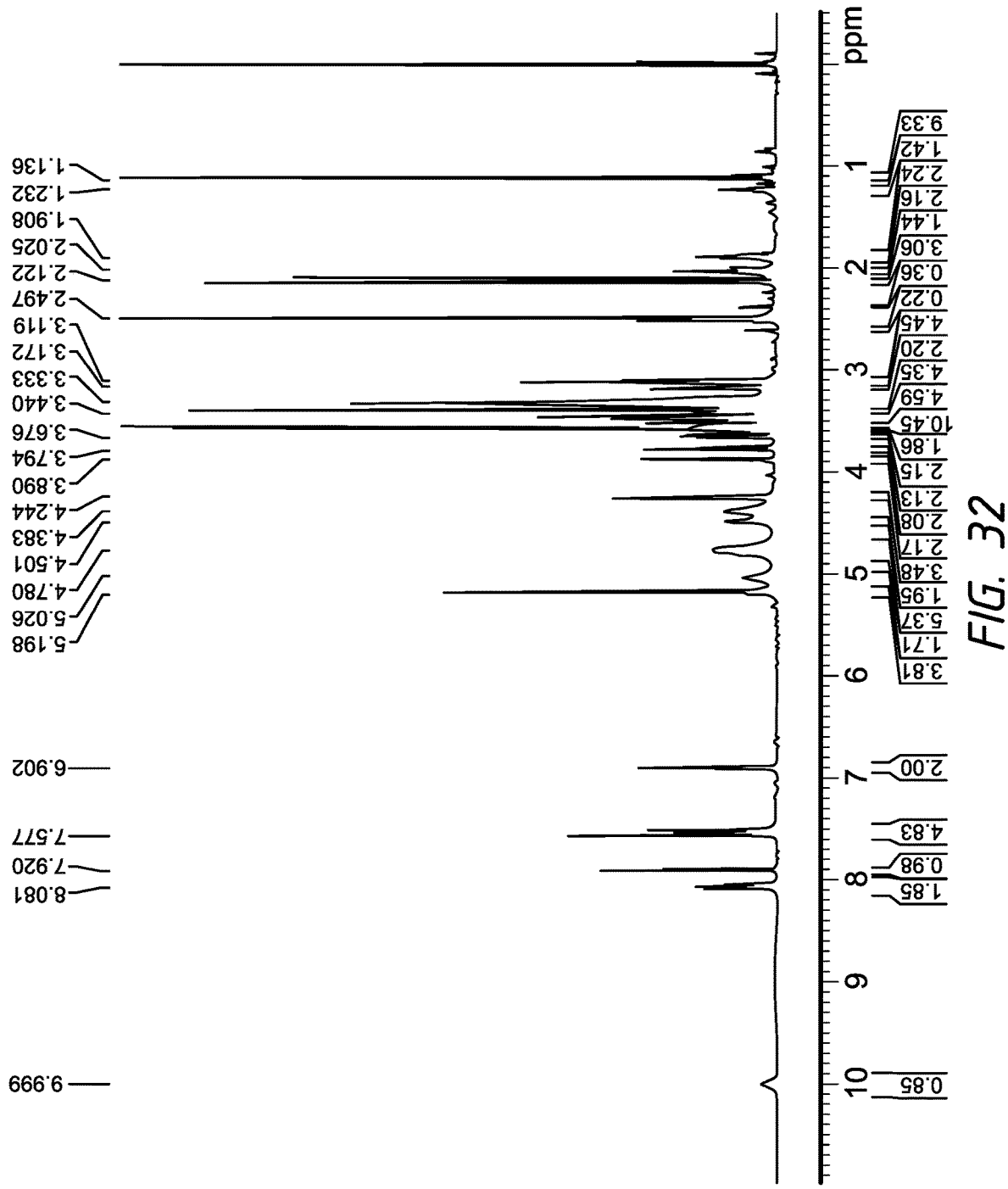
FIG. 32 is a $^1$H NMR spectra of fedratinib diHCl co-crystal with sucrose.

FIG. 32 is a $^1$H NMR spectra of fedratinib diHCl co-crystal with sucrose which indicates a 1:2 (fedratinib diHCl: sucrose) cocrystal, with a peak at 3.890 ppm from a proton of sucrose, and a peak at 6.902 ppm from two protons of fedratinib diHCl.

The above examples are set forth to aid in the understanding of the disclosure and are not intended and should not be construed to limit in any way the disclosure set forth in the claims which follow hereafter.

The invention claimed is:

1. A fedratinib diHCl co-crystal selected from a fedratinib diHCl co-crystal with succinic acid and a fedratinib diHCl co-crystal with fumaric acid.

2. The fedratinib diHCl co-crystal with succinic acid of claim 1 which is characterized by having at least 2 or more X-ray powder diffraction peaks selected from about 4.5, 9.2, and 15.6° 2Θ±0.2° 2Θ.

3. The fedratinib diHCl co-crystal with succinic acid of claim 1 which is characterized by endotherms with onset temperatures at about 118 and 207° C.±2° C., as measured by differential scanning calorimetry.

4. The fedratinib diHCl co-crystal with fumaric acid of claim 1 which is characterized by having at least 2 or more X-ray powder diffraction peaks selected from about 9.4, 11.2, and 15.8° 2Θ±0.2° 2Θ.

5. The fedratinib diHCl co-crystal with fumaric acid of claim 1 which is characterized by endotherms with onset temperatures at about 132 and 179°±2° C., as measured by differential scanning calorimetry.

* * * * *